(12) United States Patent  
Olsson et al.

(10) Patent No.: US 9,041,794 B1  
(45) Date of Patent: May 26, 2015

(54) PIPE MAPPING SYSTEM AND METHODS

(71) Applicants: Mark S. Olsson, La Jolla, CA (US); David A. Cox, San Diego, CA (US)

(72) Inventors: Mark S. Olsson, La Jolla, CA (US); David A. Cox, San Diego, CA (US)

(73) Assignee: Seescan, Inc., San Diego, CA (US)

( * ) Notice: Subject to any disclaimer, the term of this patent is extended or adjusted under 35 U.S.C. 154(b) by 0 days.

(21) Appl. No.: 14/034,293

(22) Filed: Sep. 23, 2013

Related U.S. Application Data

(63) Continuation of application No. 11/928,818, filed on Oct. 30, 2007, now Pat. No. 8,547,428.

(60) Provisional application No. 60/684,104, filed on Nov. 2, 2006.

(51) Int. Cl.  
*H04N 5/253* (2006.01)  
*G01N 21/88* (2006.01)

(52) U.S. Cl.  
CPC .................................. *G01N 21/8803* (2013.01)

(58) Field of Classification Search  
USPC ......... 348/374, 38, 84, 86; 382/107, 289, 317  
See application file for complete search history.

(56) References Cited

U.S. PATENT DOCUMENTS

| 6,999,021 B2 | 2/2006 | Taylor, Jr. |
| 7,801,425 B2* | 9/2010 | Fantone et al. ................. 396/27 |
| 2007/0135803 A1* | 6/2007 | Belson .............................. 606/1 |
| 2010/0220182 A1* | 9/2010 | Krull et al. ...................... 348/83 |

* cited by examiner

Primary Examiner — Tammy Nguyen  
(74) Attorney, Agent, or Firm — Steven C. Tietsworth, Esq.

(57) ABSTRACT

In one embodiment, a pipe inspection system includes a push-cable, a sonde coupled to the push-cable, a locator configured to receive signals from the sonde and generate positional information associated with the pipe based at least in part on the received sonde signals, a processing element configured to generate mapping information from the position information, and a non-transitory memory for storing the generated mapping information.

19 Claims, 43 Drawing Sheets

PIPE MAPPING SYSTEM AND METHODS

CROSS-REFERENCE TO RELATED APPLICATIONS

This application is a continuation of and claims priority to U.S. Utility patent application Ser. No. 11/928,818, entitled PIPE MAPPING SYSTEM, filed Oct. 30, 2007, which claims priority to U.S. Provisional Patent Application Ser. No. 60/864,104, entitled PIPE MAPPING SYSTEM, filed Nov. 2, 2006. The content of each of these applications is incorporated by reference herein in its entirety for all purposes.

FIELD

This disclosure relates generally to electronic and mechanical systems and methods for inspecting the interior of pipes and other conduits. More specifically, but not exclusively, the disclosure relates to systems for inspecting and mapping pipes using sondes in conjunction with utility locators or other related devices.

BACKGROUND

There are many situations where it is desirable to internally inspect long lengths of pipe that are already in place, either underground, in a building, or underwater. For example, sewer and drain pipes frequently must be internally inspected to diagnose any existing problems and to determine if there are any breaks causing leakage or obstructions impairing the free flow of waste. It is also important to internally inspect steam pipes, heat exchanger pipes, water pipes, gas pipes, electrical conduits and fiber optic conduits for similar reasons. Frequently, pipes that are to be internally inspected have an internal diameter of six inches or less. It is sometimes necessary to inspect several hundred feet of pipe.

In the existing art, video pipe inspection systems may include a video camera that is forced down the pipe to display the pipe interior on a video display. The inspection is commonly recorded by means of a video recorder (VCR) or digital video disk (DVD). Conventional video pipe inspection systems may include a semi-rigid push cable that provides an electromechanical connection between a ruggedized camera head assembly enclosing and protecting the video camera and a rotatable push reel used to pay out cable and force the camera head assembly down the pipe. The video push cable must be specially designed to be flexible enough to make tight turns yet rigid enough to be pushed hundreds of feet down small diameter pipe and should also incorporate electrically conductive cable having the proper conductors and impedance for conveying the NTSC or other video signals to the video display unit and for coupling to external power and ground conductors. Examples of suitable video push cables are disclosed in co-assigned U.S. Pat. No. 5,457,288 issued Oct. 10, 1995 to Mark S. Olsson and U.S. Pat. No. 5,808,239 issued Sep. 15, 1998 to Mark S. Olsson.

A conventional video pipe inspection system may include a reel inside which the video push cable is wound for storage. The reel may be supported on a frame for rotation about a horizontal or a vertical axis for paying out the video push cable and for rewinding the video push cable for storage about the reel. This may require adding a slip ring assembly into the hub and/or axle of the reel to continue electrical connections between the proximal end of the video push cable and external circuits that power the video camera head assembly and receive video signals therefrom. The usual slip ring assembly is expensive and prone to failure. The frame and axle that rotatably support the reel also represent additional bulk and expense.

The video camera head assembly design and the manner in which it is connected to the distal end of the video push cable is critical to the performance and reliability of a video pipe inspection system. These structures must be rugged, yet the camera head assembly must be compact and its manner of connection to the video push cable flexible enough to bend through tight turns. It is also desirable to incorporate an electromagnetic transmitter near the video camera head assembly to provide a radiated signal from which the camera head position may be confirmed at a remote above-ground locator instrument. Heretofore the signals radiated from such transmitters have been inherently weak, making it difficult to precisely determine the underground position of the inspection assembly with a remote locator.

Existing systems known in the art provide the operator little more than direct video image information, sometimes time-tagged by frame in recording. Most existing systems may provide a disoriented video image whenever the camera head assembly rotates away from alignment with the longitudinal axis of the pipe being inspected because of such issues as uncontrolled push cable torque or navigation through a bend or joint in the pipe. Video images from existing systems is provided with a single uniform (usually only moderate) resolution. Existing systems provide no means for tracking changes in camera orientation and distance traversed in the subject pipe or conduit nor to generate a map of the pipe from camera travel distances and headings.

Accordingly, there is an unmet need in the art for a pipe inspection system that can provide internal pipe images with accurate location and orientation information. Moreover, there is also a continuing need in the art for a pipe inspection system that can provide the location and orientation data required to provide an accurate mapping of the pipe under inspection to an operator, as well as provide other advantages.

SUMMARY

In accordance one aspect, the present disclosure describes an advantageous enhancement to pipe inspection systems by, integrating multiple local condition sensors with the camera head assembly in the pipe inspection assembly and by providing an improved information display format and system, an improved cable-counting method, and/or improved methods for detecting, analyzing and relaying data for determining camera location and environment in real time during a pipe inspection. This disclosure also describes a system and method for generating a three dimensional (3D) pipe mapping image on a display in real time from data received from a pipe inspection assembly.

Various additional aspects, features, and functions are further described below in conjunction with the appended drawings.

BRIEF DESCRIPTION OF THE DRAWINGS

The present disclosure may be more fully appreciated in connection with the following detailed description taken in conjunction with the accompanying drawings, wherein.

DETAILED DESCRIPTION OF EMBODIMENTS

Overview

This application is related by common inventorship and subject matter to the commonly-assigned patent application Ser. No. 10/268,641, filed on Apr. 15, 2004 and published on Apr. 15, 2004 as U.S. Patent Application Publication No. 2004/0070399A1, and the commonly-assigned patent application Ser. No. 10/308,752, filed on Dec. 3, 2002 and published on Apr. 15, 2004 as U.S. Patent Application Publication No. 2004/0070535A1, both of which are entirely incorporated herein by this reference.

This application is also related by common inventorship and subject matter to U.S. Pat. Nos. 5,808,239 and 5,939,679, both issued to Mark S. Olsson, and U.S. patent application Ser. No. 10/858,628, filed on Jun. 1, 2004 by Mark S. Olsson et al. and published on Dec. 15, 2005 as U.S. Patent Application Publication No. 2005/0275725A1, all of which are entirely incorporated herein by this reference.

Termination assemblies suitable for use in the proximal and distal ends of a video push cable are disclosed in U.S. Pat. No. 6,958,767 issued to Mark S. Olsson et al., which is entirely incorporated herein by this reference.

This application is also related by common inventorship and subject matter to U.S. Patent Application 2006/0006875, published Jan. 12, 2006 by Mark S. Olsson, et al., now U.S. Pat. No. 7,221,136, and U.S. Patent Application Publication No. 2005/0275725 published Dec. 15, 2005 by Mark S. Olsson et al., both of which are entirely incorporated herein by this reference.

The improvements described herein may also be implemented in a video pipe inspection system embodiment of the general type disclosed in U.S. Pat. No. 6,545,704, issued Apr. 18, 2003, and entirely incorporated herein by this reference.

Figure 1:
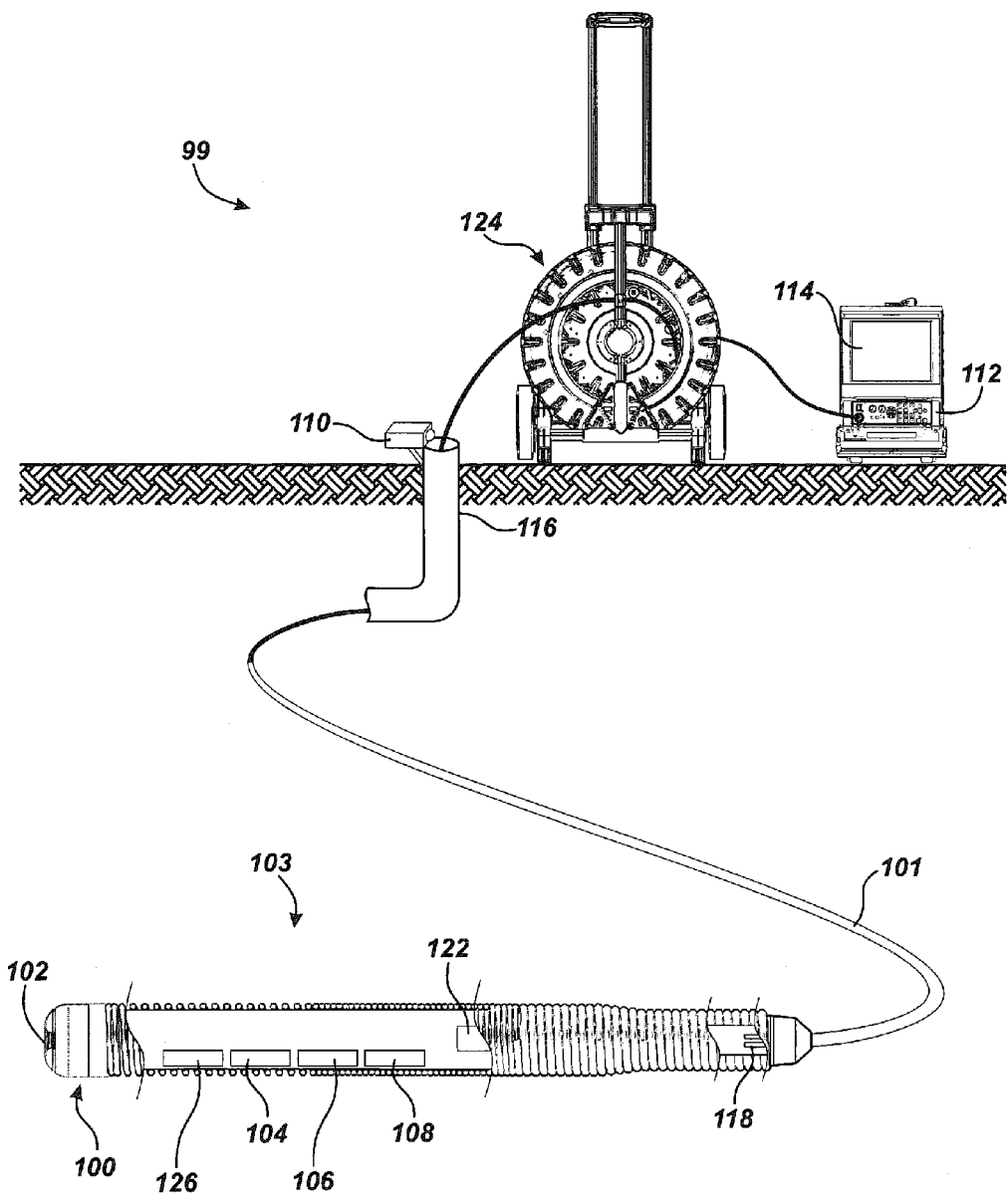
FIG. 1 is a schematic diagram illustrating an exemplary embodiment of the pipe mapping system showing a pipe inspection assembly having various local condition sensors at one end of a transmission cable coupled to a cable-counter at the pipe entry head.

FIG. 1 is a schematic diagram illustrating an exemplary pipe mapping system embodiment 99 showing a pipe inspection assembly 103 having an inspection camera head assembly 100 incorporating an image sensor 102, and also having a three-axis compass 108, a three axis accelerometer 126, a three-axis gyroscopic ("gyro") sensor 104, and a temperature sensor 106, each for producing a sensor data signals responsive to the respective local physical condition. Pipe inspection assembly is coupled to a push cable 101, which is stored and extended from the cable storage drum unit 124 proximate to a cable counter 110 for counting the length in feet or meters of push cable 101 extending into a pipe 116 under inspection. Image sensor 102 is disposed at the front of camera head assembly 100 (at the very front of inspection assembly 103) so that the field of view (FOV) of image sensor 102 includes the entire circumference of the adjacent interior pipe wall (not shown). Local condition sensor data along with video or still images of this FOV are sent back over suitable conductors (not shown) in push cable 101 to a data processor 112 and an image display 114. Gyro sensors 104 sense inspection camera rotation around each of three sensing axes. A temperature sensor 106 provides temperature at the inspection camera. Gyros are particularly useful if the earth's magnetic field is distorted by residual magnetism or adjacent ferromagnetic materials. An integral Sonde 122 is partially revealed in FIG. 1. The power and data conductors (not shown) in push cable 101 are coupled to the camera cable (not shown) by a mating plug 118 or termination.

Figure 2:
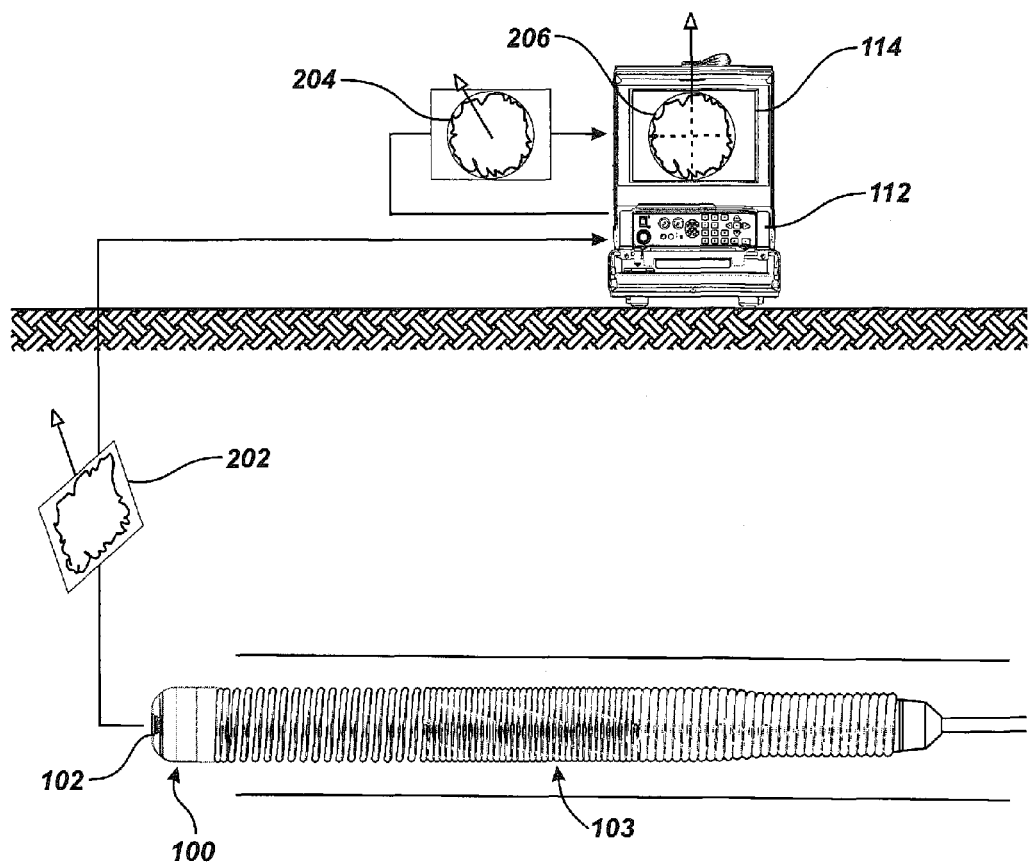
FIG. 2 is a detail diagram of the system of FIG. 1 illustrating an oblique view of a rectangular native camera head assembly image, an intermediate cropped circular processor image, and a circular "radar-scope" display image realigned with true vertical.

The rectangular image produced by an inspection camera may be cropped and reoriented to provide a circular "radar-screen" type image correctly aligned with the pipe at the display. FIG. 2 is a detail diagram of system 99 (FIG. 1) showing image sensor 102 in camera head assembly 100, which produce a raw, rectangular image 202 of the interior of a pipe (not shown) for transmission as digital information to a processor 112 wherein the image 202 is reconfigured into a circular image 204. The processor 112 then rotates image 204 to reorient it responsive to sensor data from accelerometer 126 and/or gyroscopic sensors 104 (FIG. 1). Because sensors 104 and 126 detect rotation of camera head assembly 100, these sensor signals may be used to compute the angular rotation of the camera feed with respect to the pipe under inspection. Adjusting the orientation of display image 204 responsive to these sensor data produces the correctly oriented circular "radar-scope" display image 206, which is then transmitted from processor 112 to the display unit 112. The display image 206 resulting from this process orients the pipe bottom at the display bottom independently of the camera head assembly orientation within the pipe.

Figure 3A:
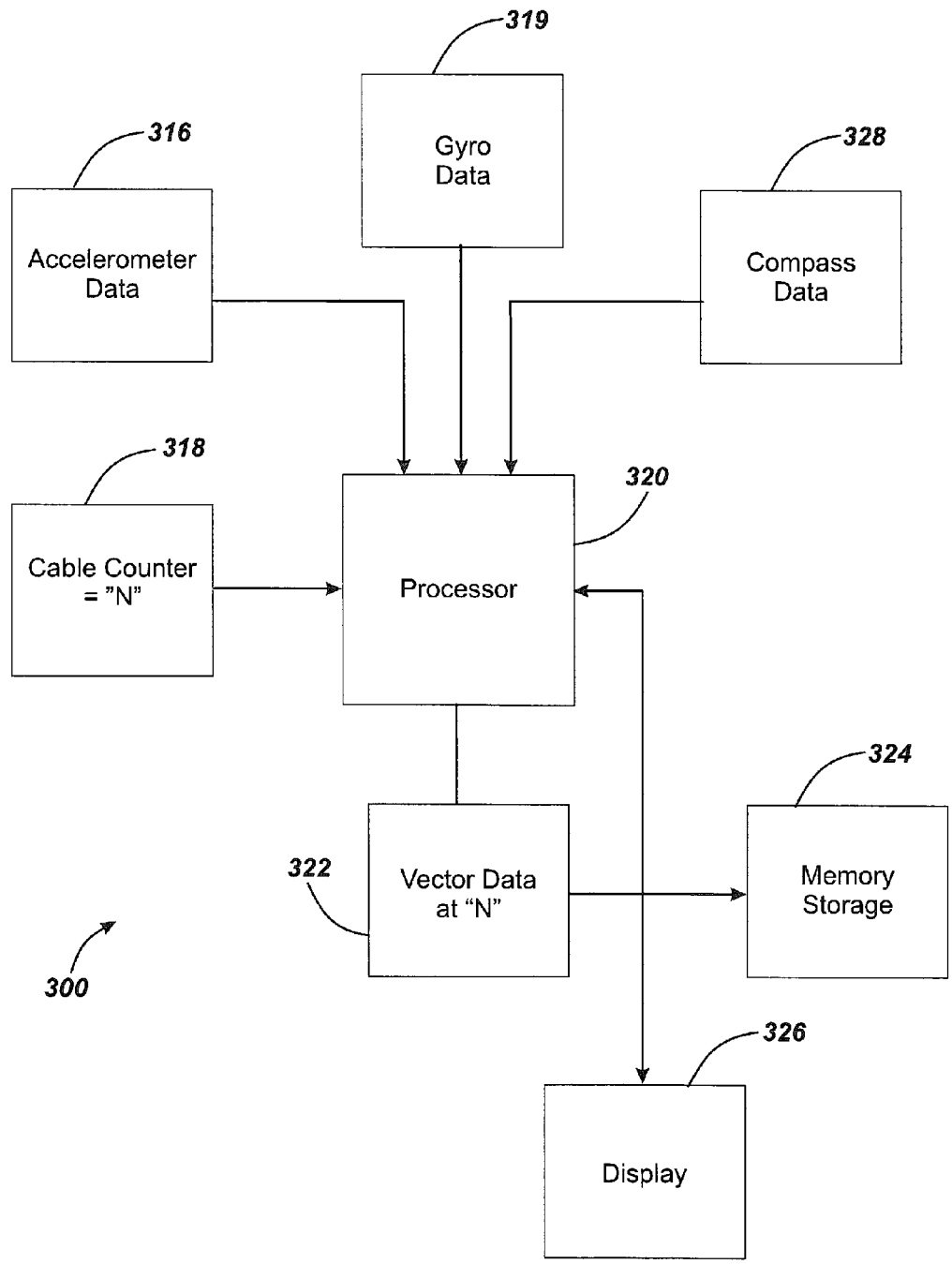
FIG. 3A is a block diagram illustrating an embodiment of the processing flow of accelerometer data, compass data, gyro data, cable counter data for the system of FIG. 1.

This disclosure is directed to a method of capturing complete pointing vector information for individual images at different instants in time that facilitates the generation of a tracking map and a three-dimensional (3D) representation of the pipe during inspection. An inspection path track image may be displayed with the camera head image, for example. FIG. 3A is a block diagram illustrating a processing flow embodiment 300 of accelerometer data 316, compass data 328, gyro data 319, and cable counter data 318. The accelerometer data 316 are combined with the magnetic compass data 328 to produce a camera head assembly pointing vector 322, which is then associated with the current cable counter step increment 318. It may be reasonably assumed that the inspection camera pointing direction is approximately parallel with the axis of the pipe under inspection when moving therein. A cable counter value 318, accelerometer data 316, gyro data 319, and compass data 328 are sent to the system data processor 320, which responsively produces a pointing vector value 322 indexed to footage counter output (N) 318. The pointing vector value 322 is integrated by the processor 320 into a composite image for the video display 326 and the data are also stored in the memory 324, which may be embodied as volatile, nonvolatile, or a combination thereof.

Figure 3B:
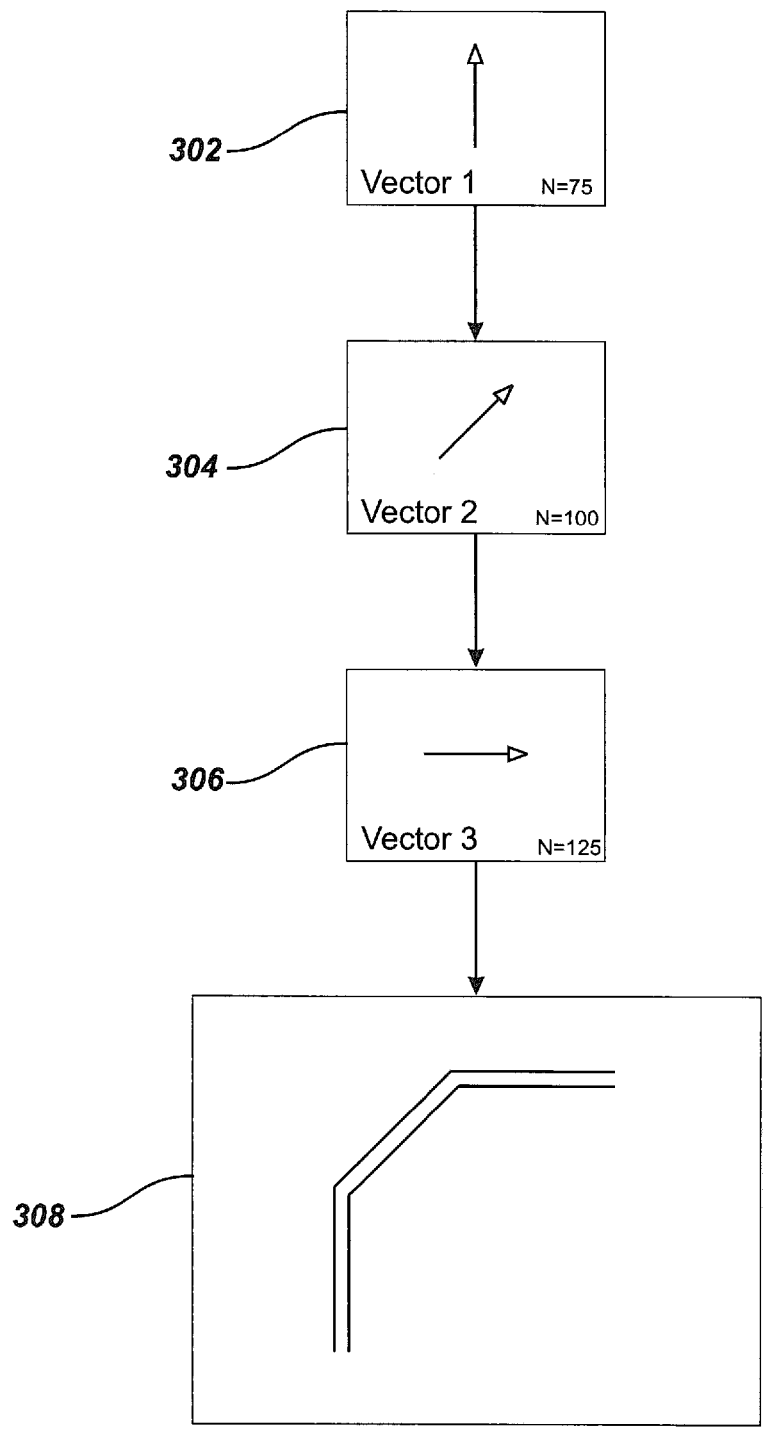
FIG. 3B is a schematic diagram illustrating an embodiment of the processing flow of several cable count and pointing vector data layers to form a composite path representing a camera trajectory through a pipe under inspection for the system of FIG. 1.

Camera motion vectors represent a combination of speed and time and therefore length traveled. Motion vectors may be accumulated using a fixed time interval between data samples over a varying length, or by using fixed lengths between data samples over varying intervals or some combination of the two methods. FIG. 3B is a schematic diagram illustrating a motion vector processing embodiment. If the length of each of these pointing vectors is set to the distance that the inspection cameras moves, which corresponds to each cable-counter step increment, then linking this series of motion vectors end to end provides a map of the approximate inspection camera trajectory through the piping system under inspection. In FIG. 3B, several exemplary motion vector values 302, 304, and 306 are combined in the processor 320 (FIG. 3A) to form a composite camera path 308, which may be displayed on an inset window on the image display 326 (FIG. 3A) or as a video image overlay. By this process, a 3D map of the piping path may be created simply by sampling camera motion vectors while passing the inspection camera through the piping system under inspection. Any useful display known in the art is suitable for displaying the piping path image to the inspection operator.

Figure 3C:
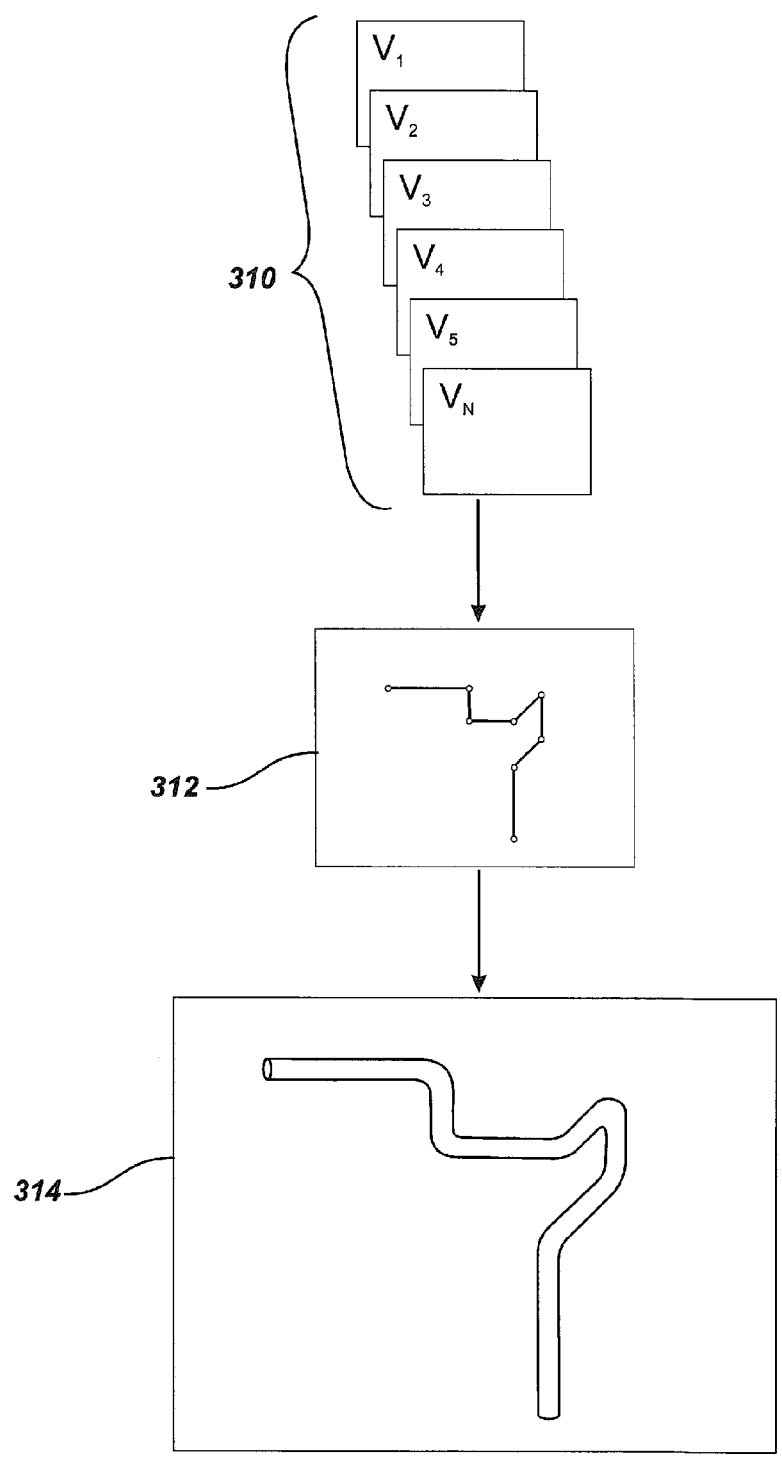
FIG. 3C is a schematic diagram illustrating the merger of a trajectory map sequence to form a 3D image of a piping system for the system of FIG. 1.

FIG. 3C is a schematic diagram illustrating the merger of a trajectory map sequence to form a 3D pipe system map image. A series of motion vector data 310 are integrated into a trajectory map 312 and are then combined with additional local condition sensor information to produce a 3D integrated drawing 314 of the pipe system as it has been traversed.

Figure 3D:
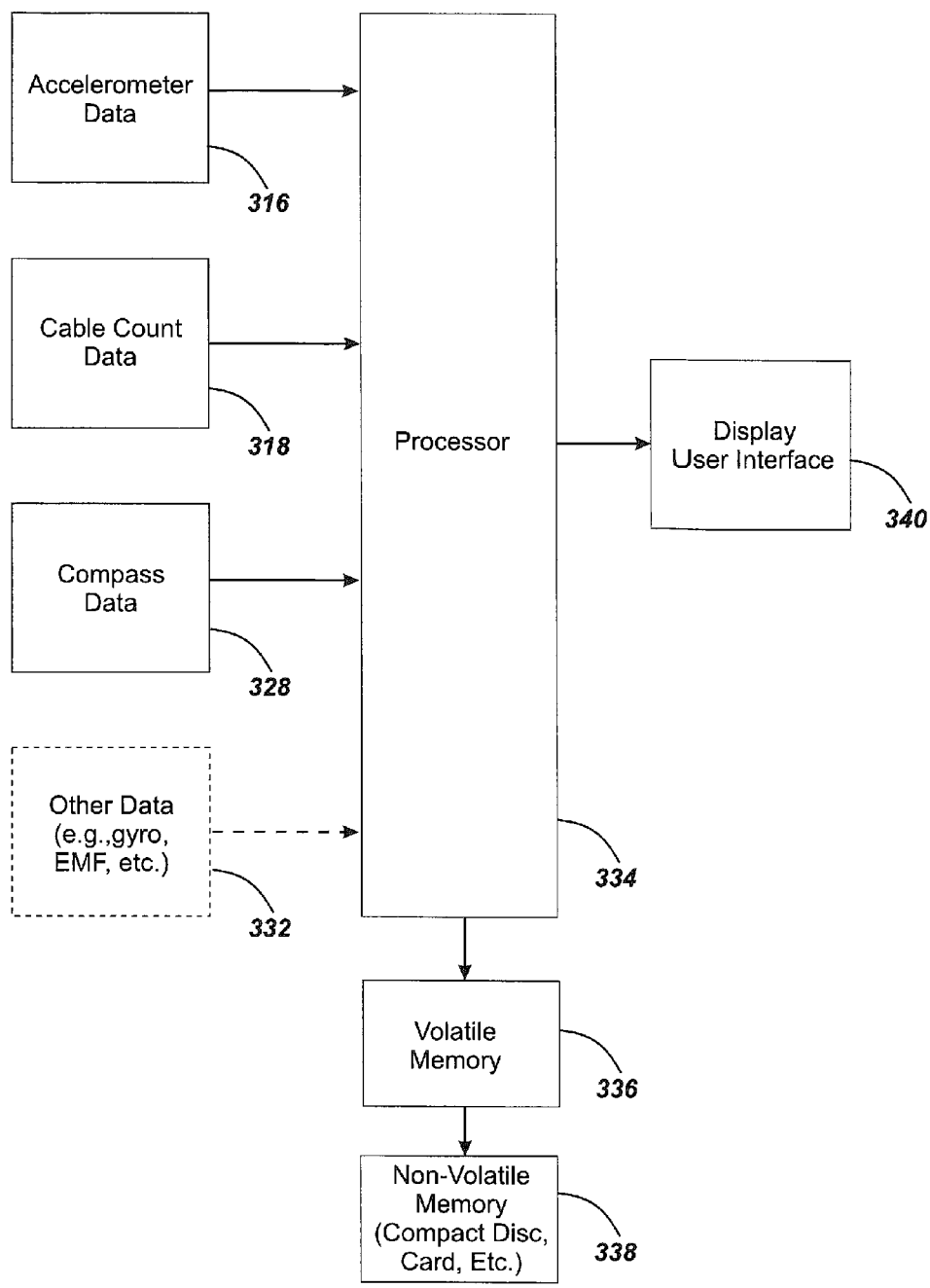
FIG. 3D is a schematic diagram illustrating the transfer of pipe mapping data between a processing and display unit and a local data store/remote data store for the system of FIG. 1.

The pipe mapping data may be stored by any known means and subsequently retrieved for later viewing or evaluation. FIG. 3D is a schematic diagram illustrating the transfer of pipe mapping data between a processing and display unit and a local data store/remote data store. The accelerometer data 316, cable count data 318, compass data 328, and other sensor data 332 are sent to the data processor 334, which loads the data into volatile memory storage 336, manages the writing of the data to non-volatile memory 338 (for example, a flash memory unit, card, disk or the like) and assembles display updates for implementation in the display 340. These pipe mapping data may be added information to a Geographical Information System (GIS) Database of known utility locations, for example, to improve future locate operations and reduce the risk of accidental damage to the pipe from excavation at the wrong location.

Figure 4:
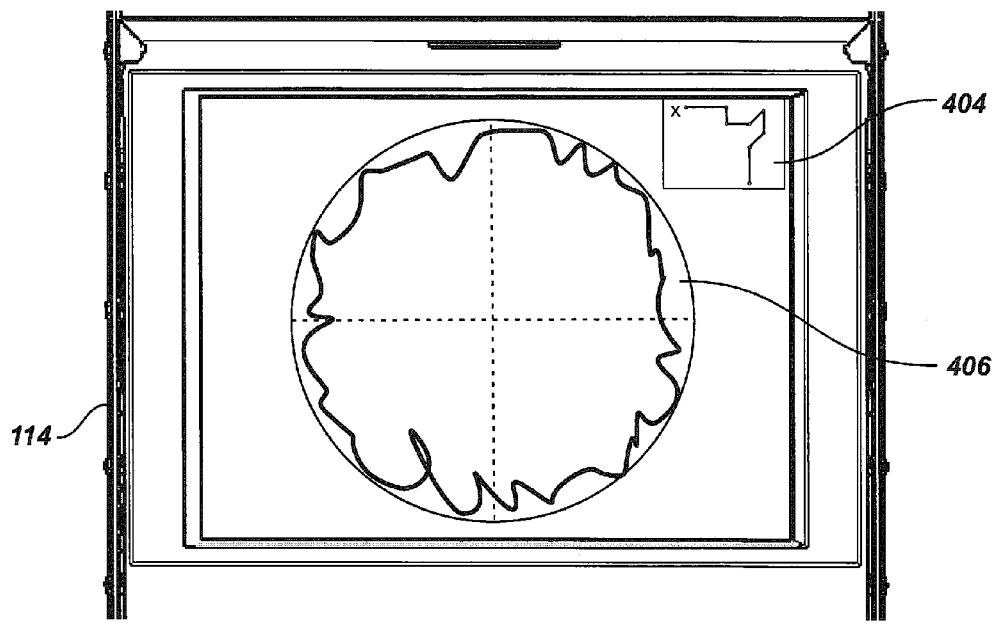
FIG. 4 illustrates a screen display image suitable for representing a pipe inspection camera image together with a second embedded image frame showing camera track display image.

FIG. 4 illustrates a screen display image suitable for representing a pipe inspection camera image together with a second embedded image frame showing the real time camera track display image. The system display screen 114 shows a centrally located circular image 406 portraying the camera view corrected for the inspection assembly roll orientation deduced from accelerometer or gyro data. A small display window 404 portrays the 2D camera track as it is composited in real time. Alternatively, small display window 404 may show a 3D image of the pipe map instead of or in addition to the 2D track.

Figure 5A:
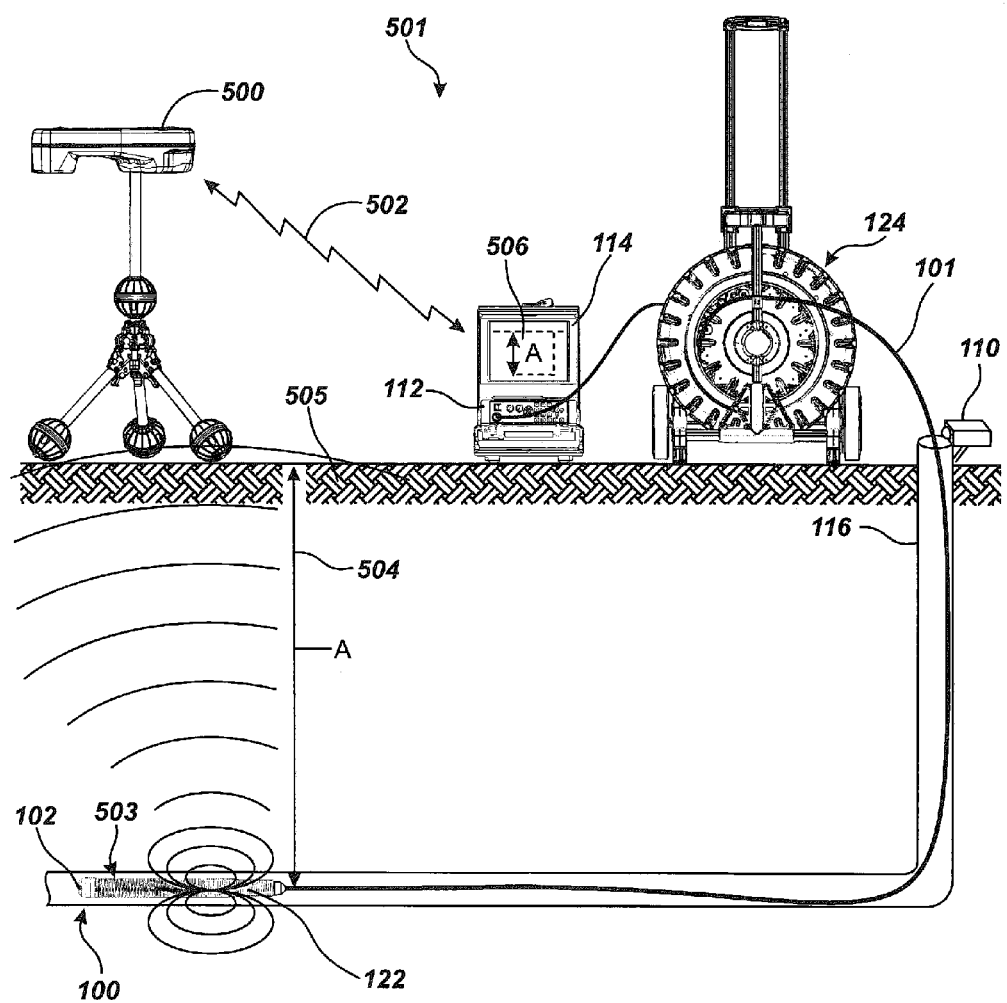
FIG. 5A is a schematic diagram of a pipe mapping system embodiment illustrating the detection of an integral Sonde during pipe inspection.
Figure 5B:
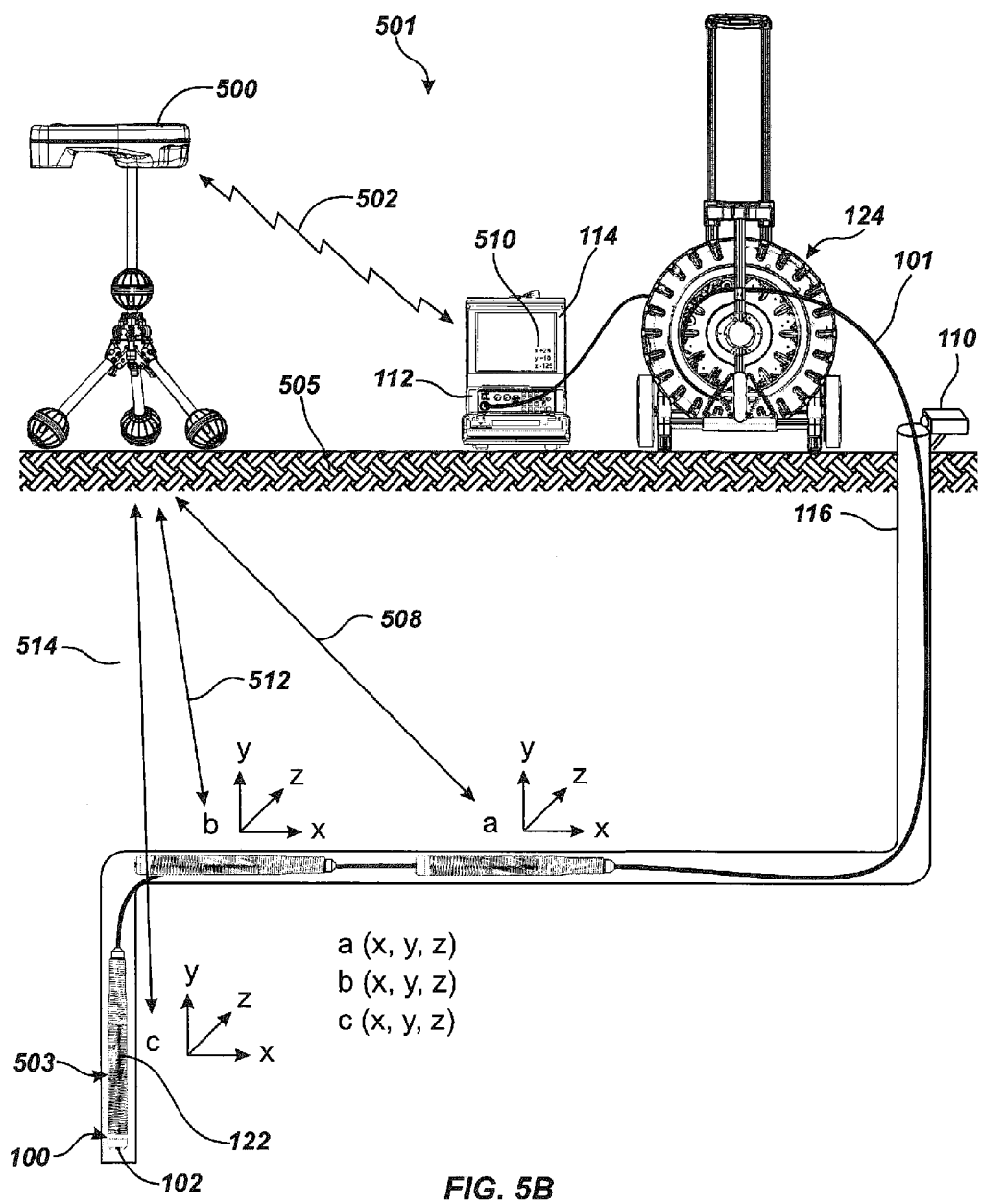
FIG. 5B shows the scene from FIG. 5A modified to illustrate tracking of an integral Sonde through a bend during pipe inspection.

The system of this the disclosure is directed to may include a dipole Sonde attached to or near the inspection assembly or integrated therewith to facilitate operator measurement of camera depth below ground at any moment. FIG. SA is a schematic diagram of a pipe mapping system embodiment 501 in which the depth (A) 504 of the inspection assembly 503 below some reference surface, such the earth's surface 505, is measured by using an electromagnetic Sonde locator 500 to locate a Sonde 122 in or adjacent to the inspection camera head assembly 100. The locator's computed measurement depth (A) 504 from ground level 505 to the integral Sonde 122 is shown. Locator 500 is disposed at the ground level 505 above a buried pipe 116 in which a push-cable 101 affixed to the inspection assembly 503 incorporating the integral Sonde 122 and camera head assembly 100 with image sensor 102 (FIG. 1) is disposed as it is during inspection of pipe 116. A removable cable count device 110 is affixed to the head of pipe 116. The processor unit 112 and display unit 114 are illustrated as being disposed on the far side of the cable storage drum unit 124. In this configuration, for example, the locator 500 detects inspection assembly 503 at the distal end of cable 101 and computes the depth value (A) 504. Information from the locator 500 is sent to the processor unit 112 through the wireless data link 502. The information sent to the display 114 may include the detected depth (A) 504 for use in rendering the tracking map 506, for example. The 3D track of the camera head assembly may also be measured by a locator, and these measurements transmitted to the camera controller. Alternatively, the camera track information measured by the camera control unit from local condition sensor and cable-count may be sent to the locator by wire or wireless means. FIG. SB shows the scene from FIG. 5A modified to illustrate tracking of an integral Sonde 122 through a bend during pipe inspection and illustrates three Sonde positions (a, b, c). Data are transmitted wirelessly from locator 500 to processing unit 112 and display unit 114 through link 502 using a data transfer protocol such as IEEE 802.15.4, for example. Depth values 508, 512 and 514 for the respective illustrated Sonde positions (a, b, c) are each displayed as text lines exemplified by the text line 510 on the display 114. The locator 500 may be moved through a series of search and detection locations selected according to the detected motion of the inspection assembly 503. Depth values are computed by the locator for the three illustrated positions of the inspection assembly 503, and reported for presentation as a text line 510 on the display 114 based on signal detection (X, Y, Z), sonde position and orientation (not shown), and depth computation at the locator 500 or of processor 112.

Figure 6:
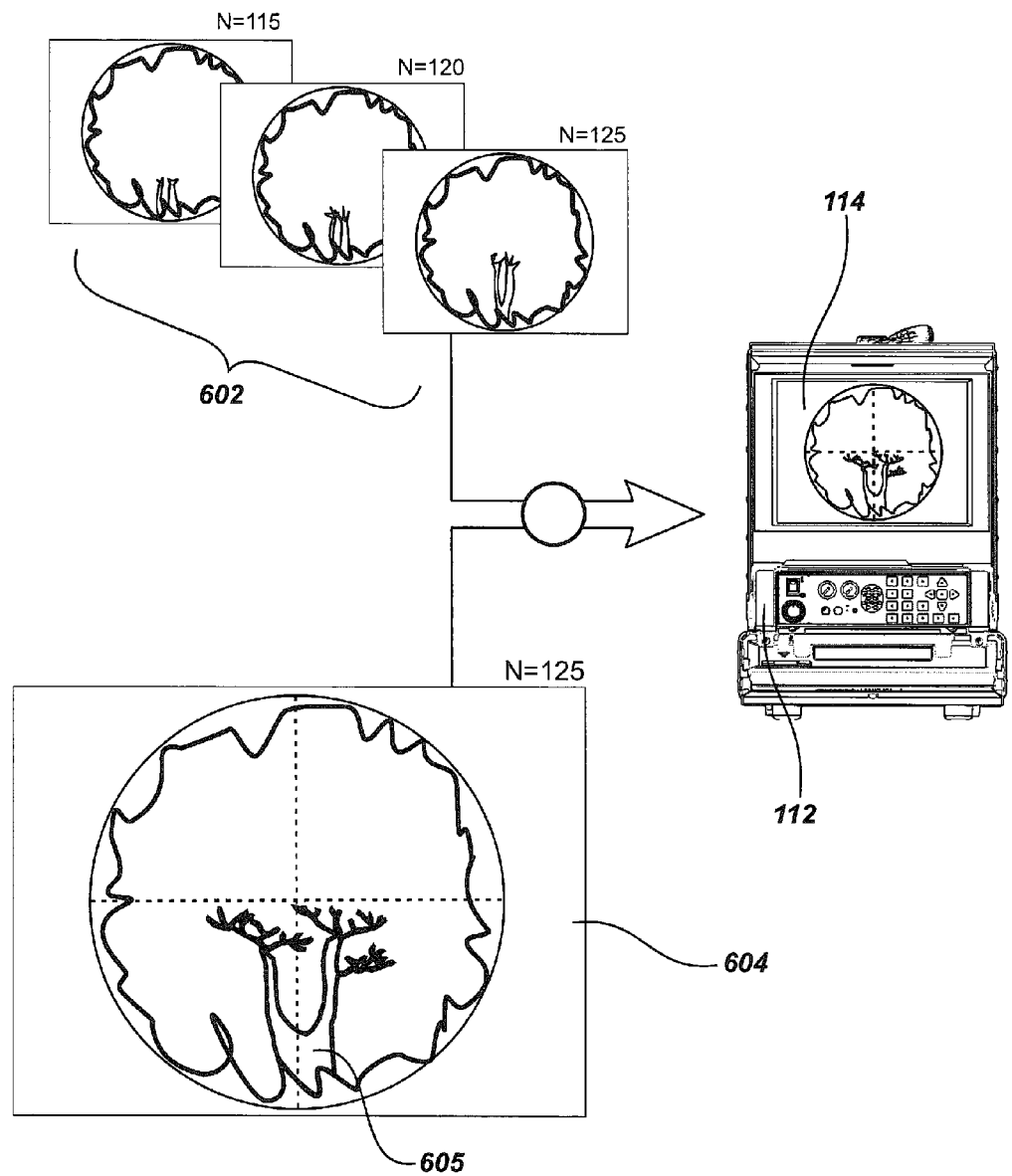
FIG. 6 illustrates the selection for display from a series of video images and a high resolution still image under manual or processor control in a pipe mapping system embodiment.

The system of this the disclosure is directed to may include means for automatically or manually switching the camera head image from low resolution display (for example, while the camera is moving) to high-resolution display (for example, when the camera stops moving) to provide improved opportunity for detailed inspection. FIG. 6 illustrates the selection for display of a high resolution still image 604 from a series 602 of video images under manual or processor control.

The camera head assembly includes an imager that can send images in either of video format or higher resolution sequential still images. The system's image transmission bandwidth may be devoted to high frame-rate transfer of low-resolution images, or low frame-rate transfer of high resolution images, depending on camera motion or operator preferences. The particular images transmitted by the camera head assembly 100 may be selected by manual operator control or by automated means responsive to changes in camera head assembly motion, such as switching of higher-resolution images when the inspection assembly 503 stops moving. Changes in image transmission characteristics may be automatically controlled by either the camera head assembly 100 or by the data processing and image display system 112 in cooperation with the camera head assembly 100. Motion changes may be detected in data from accelerometer 126 (FIG. 1) or from the image data changes or any useful combination thereof. A higher resolution image may be transmitted for display and/or storage whenever the camera head assembly motion halts. The inspection camera operator viewing the display perceives this higher-resolution as a sharper and more detailed view of the camera FOV whenever pausing camera motion through the piping system under inspection. This enhanced view is presented seamlessly without operator action beyond pausing camera head assembly motion. High-power strobe LEDs (not shown) are useful for illuminating the camera FOV for synchronous high-resolution imaging, for example.

The direction and distance of integral Sonde motion may be determined from the Sonde detection by an advanced Sonde locator; such as, for example, the locator disclosed in U.S. Pat. No. 7,009,399B2 issued to Mark S. Olsson, et al. and entitled "Omnidirectional Sonde and Line Locator," which discloses an electromagnetic locator 30 that may include a GPS receiver as described at Col. 13, lines 59-61, the content of which is entirely incorporated herein by this reference. The resulting Sonde locate data may be used to improve the pipe mapping accuracy by augmenting existing data from compass and accelerometer sensors in environments where these sensors are less accurate, such as in the presence of certain large ferromagnetic bodies, for example.

FIG. 6 illustrates a series of low-resolution images 602, each of which is associated (labeled) with a different cable-count tag represented by the value (N) shown in feet or meters, for example. In this example, the images 602 represent the camera FOV as it approaches a root 605 that has penetrated the pipe wall. The forward motion of the camera is paused, at N=125, whereupon the image transmission may switch to the high-resolution image 604 shown, to facilitate improved inspection and evaluation. This automatic switch to high-resolution imaging may be manually controlled via external switch or processor controlled based on a pause in motion detected via an accelerometer or other motion detector through the pipe, for example.

Figure 7A:
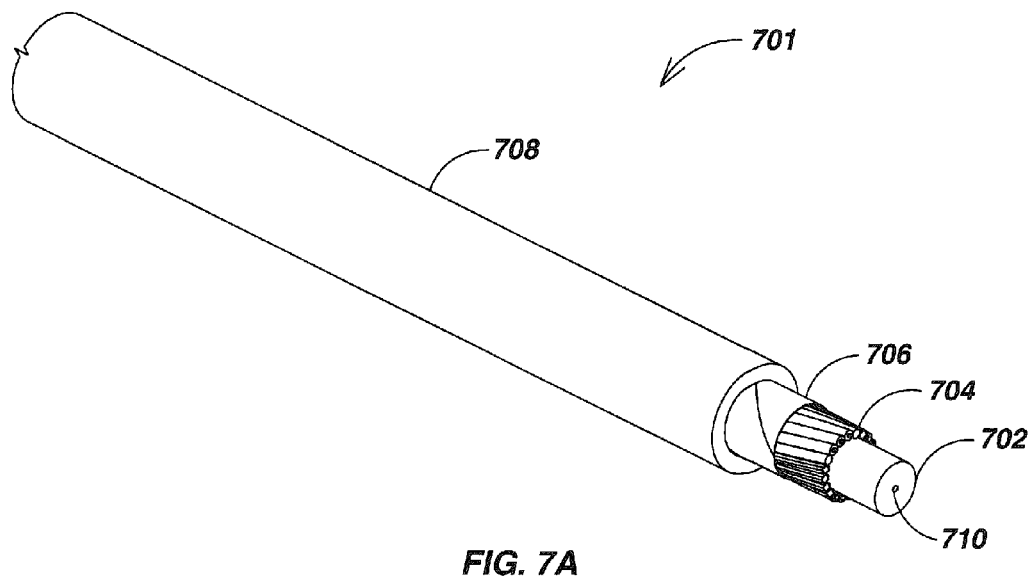
FIG. 7A is an oblique cut-away view of a system push-cable embodiment having a composite core surrounded with power and/or data conductors and having an optional central optical fiber for transmitting optical data signals; [0029]
Figure 7B:
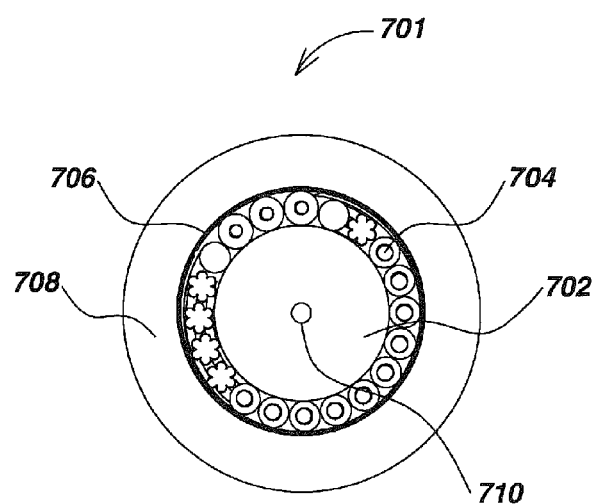
FIG. 7B is a cross-sectional view of the system push-cable of FIG. 7A.

The system of this the disclosure may include a push-cable used in inspection formed around a resilient composite rod core with a central glass or plastic optical fiber for transferring optical data representing images and local condition sensor data to a processor and a display system. FIG. 7A is an oblique cut-away view of a system push-cable embodiment 701 having a composite core 702 surrounded with power and/or data conductors 704 and having, for example, a central optical fiber 710 for transmitting optical data signals. One or more optical data transmission fibers exemplified by the fiber 710 may be placed near the central axis of the resilient composite rod 702 inside inspection camera system push-cable 701. Optical fiber 710 is useful for transmitting high-resolution imaging data and other information from the inspection assembly 103 to a data processor 112 and image display 114 (FIG. 1). FIG. 7B shows a detailed cross-sectional view of the push-cable 701 with the composite (e.g., fiberglass) core 702 having a centrally embedded fiber-optic cable 710 surrounded by other data and/or power conductors (e.g., 704) wrapped in a shielding layer 706 and all enclosed by a resilient outer protective covering 708.

Figure 8:
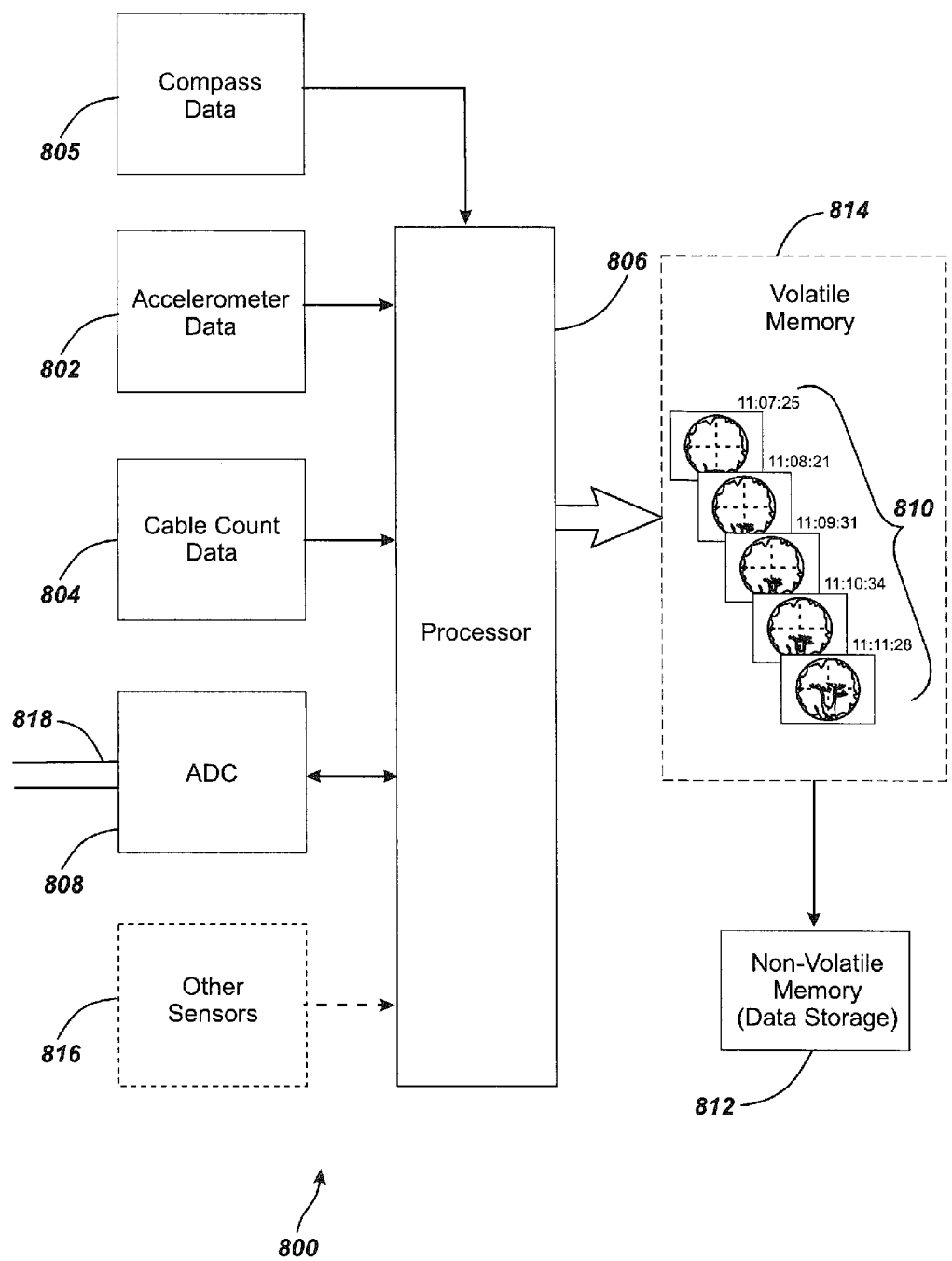
FIG. 8 is a schematic diagram illustrating an embodiment of the processing flow of cable counter, accelerometer, compass, and camera data to form a series of digital images for a pipe mapping system embodiment.

Another data processing system embodiment produces a series of time-tagged digital images combined with data from the accelerometer, compass and other sensors to facilitate computation of a relative motion estimate and an analysis of the relationship between images. FIG. 8 is a schematic diagram illustrating a processing flow embodiment 800 for forming a sequence of digital images 810 representing a combination of cable counter data 804, accelerometer data 802, compass data 805, and camera image data on fiber optic cable 818. A continuous digital strip image of the inside of the pipe under inspection is generated by the data processing system 112 as the camera head assembly 100 is pushed through the piping system under inspection (FIG. 1). The accelerometer and cable-counter data 802 and 805 are useful for estimating the relative camera motion with respect to the piping system to assess the spatial relationship of the images within the sequence 810. Images from fiber optic cable 818 are channeled through an analog to digital converter (ADC) 808 to the data processor 806. Additional data from a cable-counting means 804, an accelerometer 802, and a plurality n of other sensors 816 are combined in the processor 806 to generate the sequence of images 810, which are time-tagged and linked with other appropriate data, temporarily maintained in a volatile memory 814, and ultimately written to a non-volatile data store 812.

Figure 9:
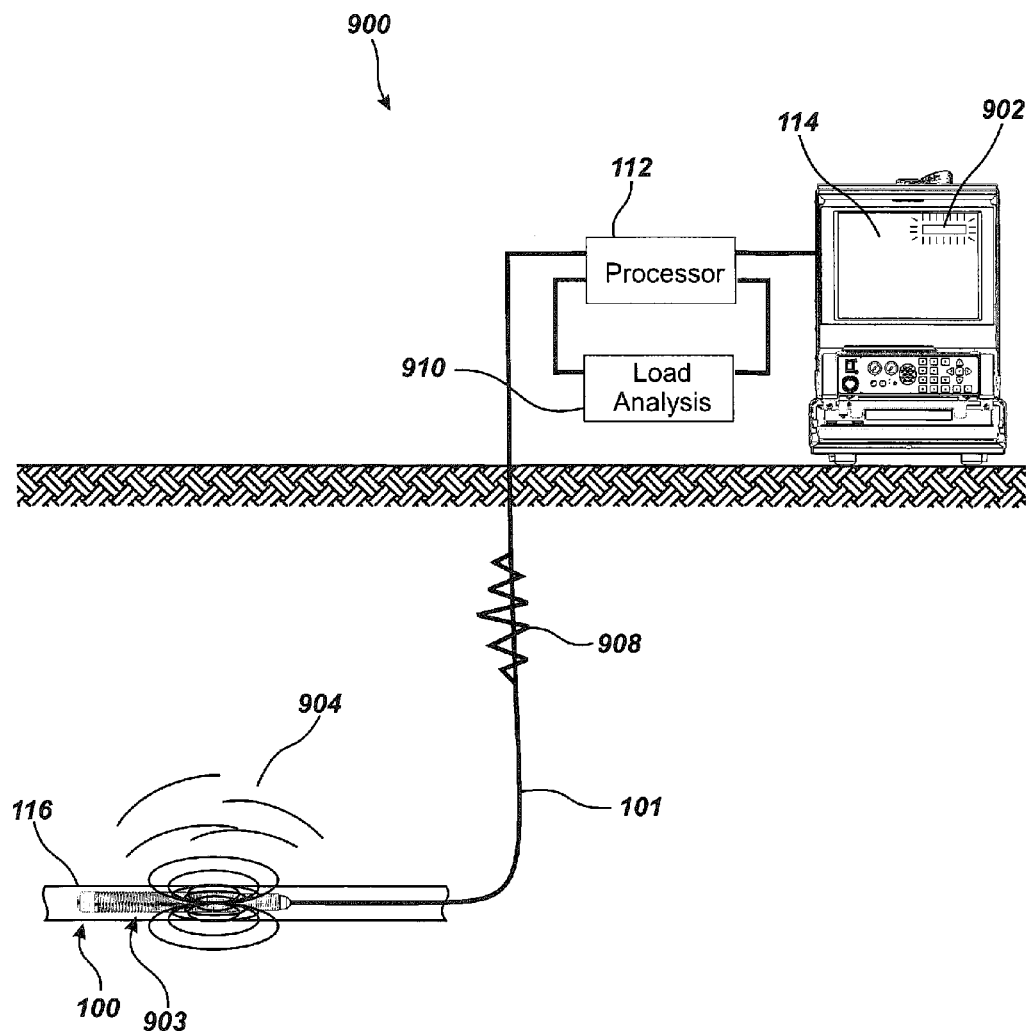
FIG. 9 is a schematic diagram of a pipe mapping system embodiment illustrating the processing flow of Sonde drive-circuit loading data to display ferromagnetic pipe properties.

The complex load impedance of the Sonde drive circuit may be employed to facilitate detection of local ferromagnetism in the piping material. FIG. 9 is a schematic diagram of a pipe mapping system embodiment 900 illustrating the processing of Sonde drive-circuit loading data to produce a display of pipe ferromagnetism. The display system 114 provides a visual indicator 902 when the system detects ferromagnetism in the pipe. In system 900, the loading or phase shift of the electromagnetic Sonde drive circuit (not shown) may be analyzed for evidence of ferromagnetic loading of the Sonde output radiation. This drive circuit output impedance analysis may be calibrated and/or verified with, for example, any data from the electronic compass sensor 108 (FIG. 1) or any other useful evidence suggesting local magnetic perturbation. The display system 114 may provide any useful visual indication of local ferromagnetism (e.g., a pipe symbol 902 may be changed from yellow to red). An inspection assembly 903 incorporating a camera head assembly 100 and a Sonde is urged by a push cable 101 into a pipe 116 under inspection. The Sonde electromagnetic dipole field 904 interaction with the local radiation impedance presented by the pipe 116 and other local elements gives rise to Sonde driver output load magnitude and phase changes 908 in the usual manner. These changes 908 are measured and analyzed by a load analysis subroutine 910 in the processor 112. The indicator 902 on the display 114 provides the operator with a ferromagnetic environment signal, for example, based on the dynamic load analysis.

In another embodiment, a Sonde and camera head assembly are coaxially disposed within the inspection assembly, wherein one or more sensors that can detect the Sonde's emitted signal frequency are disposed axially at a known distance from the Sonde to provide a signal change detection when the camera head assembly turns with respect to the Sonde axis, and also to provide an indication of changes in local electro-conductive and/or ferromagnetic characteristics.

Figure 10A:
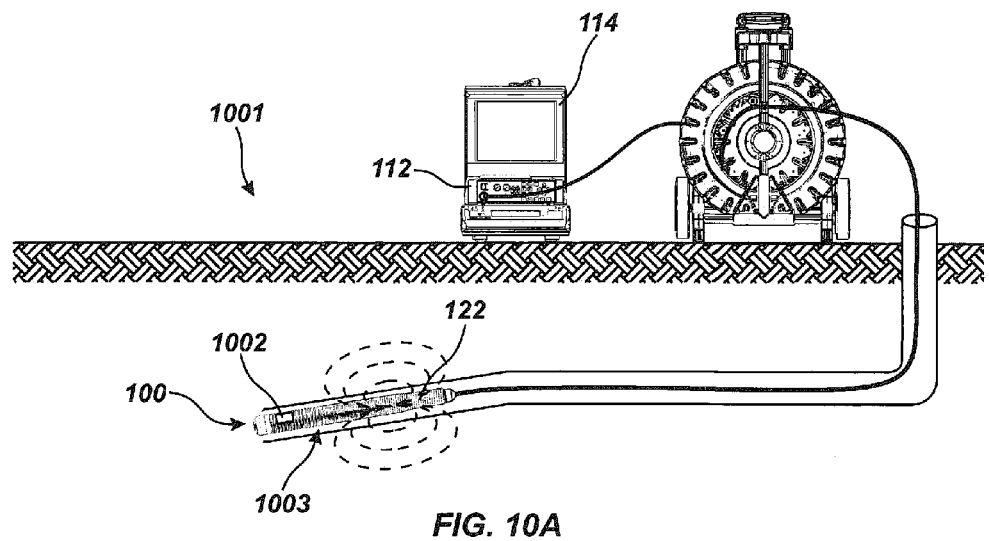
FIG. 10A is a schematic diagram of a pipe mapping system embodiment illustrating a length of cable with a EMF sensor revealed in the inspection assembly, and the integral Sonde at a known distance, with the camera head assembly and sensor axially aligned relative to the Sonde.

In another embodiment, a high-frequency locating signal emitter is coupled to the camera push cable such that the signal may be activated and deactivated by the operator or by automatic processor control, thereby providing a traceable signal for facilitating detection of the path and depth or distance of the cable emitter as an aid in mapping the conduit or pipe. FIG. 10A is a schematic diagram of a pipe mapping system embodiment 1001 having an inspection assembly 1003 incorporating the camera head assembly 100, and an EMF sensor 1002, with an integral Sonde 122 disposed at a known distance from sensor 1002. Sonde 122 is disposed substantially coaxial to the inspection assembly axis of symmetry and is displaced along this axis from the inspection camera by a fixed predetermined distance. When the camera head assembly 100 turns off of the inspection assembly axis, changes in the Sonde signal strength at sensor 1002 may be used to detect this turning motion, as well as any changes in local ferromagnetism. Alternatively, the Sonde drive circuit (not shown) may be periodically re-tuned to reflect compass sensor data output. In FIG. 10A, the inspection assembly 1003 is equipped with the integral Sonde 122 and electromagnetic sensor 1002 adapted to sense the dipole field generated by the Sonde 122, is disposed at a known distance from the Sonde 122. The inspection assembly 1003 is situated in a straight segment of pipe with the result that Sonde 122 and the sensor 1002 are coaxially disposed.

Figure 10B:
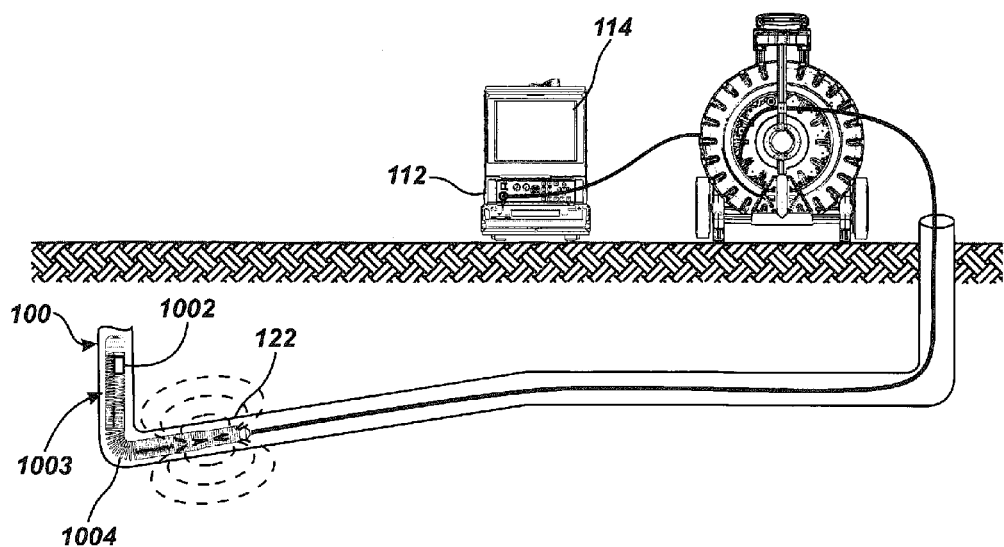
FIG. 10B illustrates the separation of the EMF sensor and Sonde in a pipe bend for the system of FIG. 10A.

FIG. 10B shows how the alignment of the Sonde 122 and sensor 1002 changes responsive to bending of the flexible inspection assembly 1003 during movement through a bend 1004 in the pipe under inspection. This realignment is reflected in the modulation of a signal produced by the sensor 1002, which is processed at the processing unit 112 to produce a corresponding change in the display 114. A change in signal from the Sonde 122 as measured at the sensor 1002 also occurs responsive to changes in the ferromagnetic or electro-inductive properties of the environment adjacent to the inspection assembly 1003, such as changes occurring during transition from nonmagnetic ABS pipe to ferromagnetic iron pipe, for example.

Figure 11:
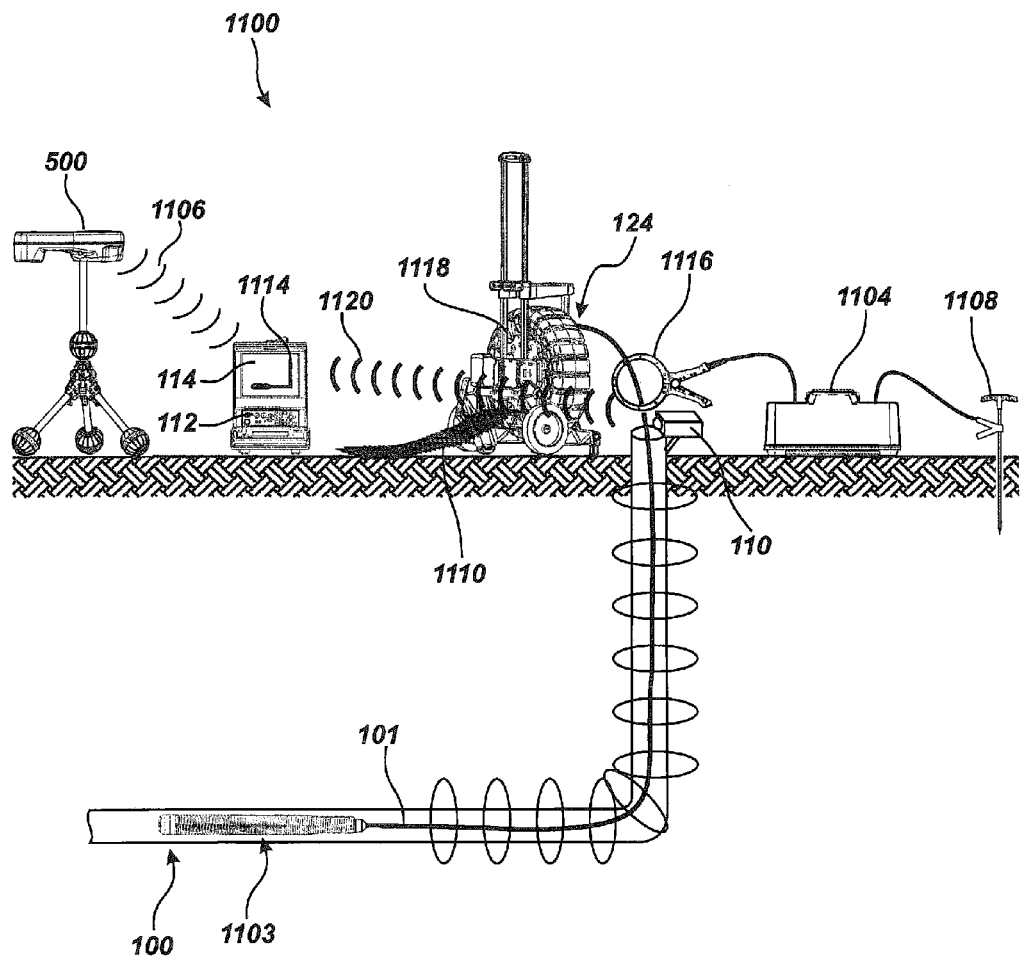
FIG. 11 is a schematic diagram of a pipe mapping system embodiment illustrating the camera cable emanating an injected locating frequency and a locator above ground being used to measure the location of the inspection assembly.

FIG. 11 is a schematic diagram of a pipe mapping system embodiment 1100 wherein the camera push cable 101 radiates an EM signal arising from an injected high-frequency (HF) locate signal. A locator 500 above ground is used to measure the location of the camera head assembly. Data from the locator 500 are wirelessly transmitted to the processor 112 on link 1106. A cable-counter 110 is disposed at the pipe entrance to sends cable indexing data to the processor 112. An external transmitter 1104 and an inductive clamp 1116 may be used to inject the HF locate signal but any other useful signal injection means known in the art may be used for this purpose. The injected HF signal may be continuous wave (CW) or activated and deactivated under manual operator or automatic processor control. The HF signal current may be measured and the measured current value used, in combination with the deployed cable length from cable counter 110, to infer useful information about the electromagnetic properties of the piping system under inspection. The inspection assembly 1103 is shown at the end of a push-cable 101, which emerges from a pipe entry point supplied with a removable cable-count means 110. The cable may be connected by inductive clamp 1116 to an external transmitter 1104 whose other terminal is attached to a ground stake 1108.

Alternatively, another useful injection embodiment directly couples a transmitter 1118 built into the cable storage drum assembly 124 to the push-cable 101. The cable drum 124 may be fitted with a built-in line-locating transmitter 1118 and an innovative grounding device in the form of a metallic grounding mat 1110. FIG. 11 shows this alternative grounding method, which is suitable for hard surfaces, such as concrete pads, where a ground stake cannot be used. Grounding mat 1110 is connected electrically to the built-in transmitter 1118. The grounding mat 1110 may be rolled up for storage when not in use and consists of a metallic cloth of chainmail or similar construction that is flexible and sufficiently dense to provide ground contact when spread out. A line locator 500, preferably of a self-standing type, is used to detect the location of the energized push-cable 101 by tracing the injected signal frequency. Data from the locator 500 are transmitted by wireless link 1106 to the pipe inspection system processor 112 and processed to render the image 1114 on the display unit 114. Optionally, camera data can be sent from cable drum 124 to display unit 114 by wireless link 1120.

Figure 12A:
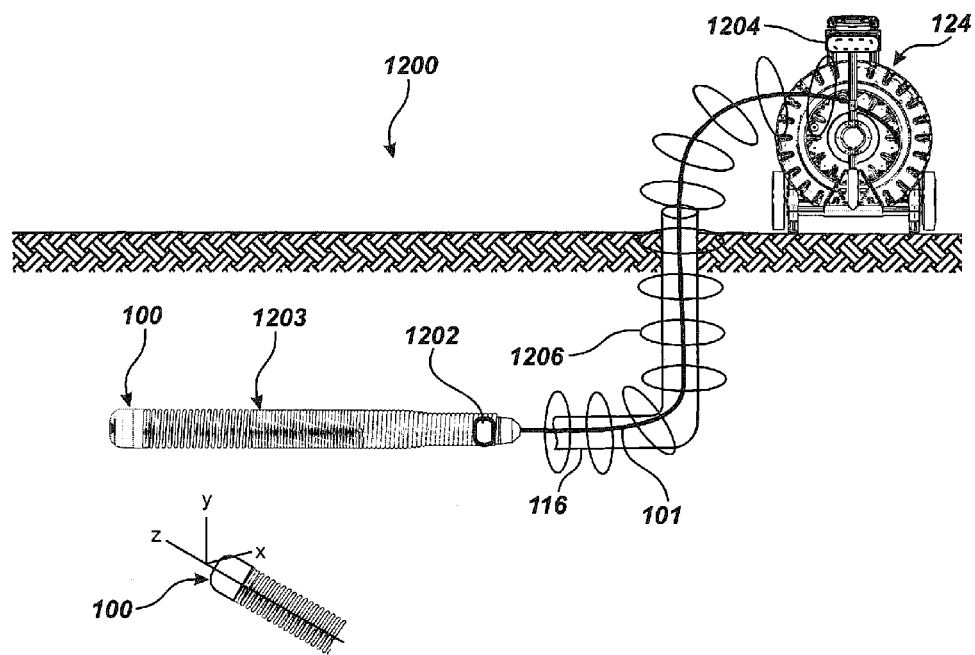
FIG. 12A is a schematic diagram of a pipe mapping system embodiment illustrating a inspection assembly with EMF sensor axially aligned with the cable to which a locating frequency has been coupled using a built-in transmitter.
Figure 12B:
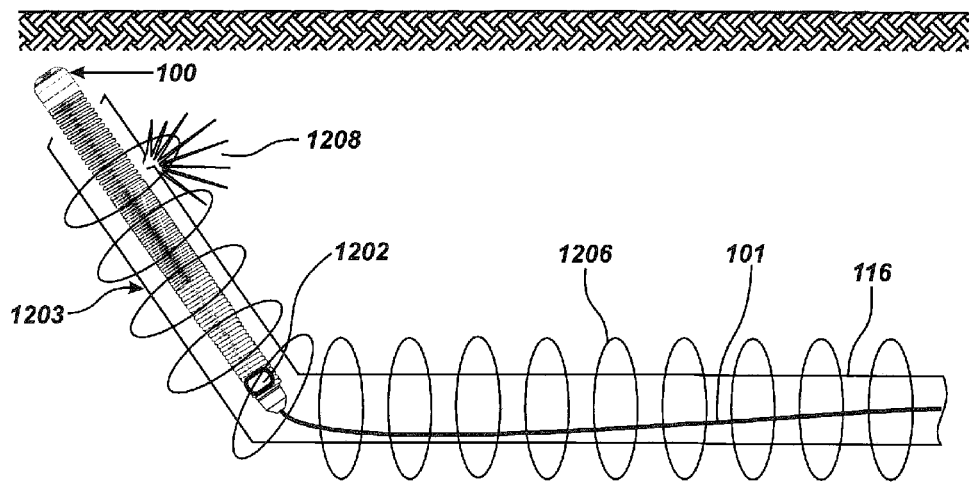
FIG. 12B shows the inspection assembly of FIG. 12A with the cable and EMF sensor unaligned within a leaky bent pipe.

In another aspect of this embodiment, an electromagnetic field (EMF) sensor for the locating signal frequency of the transmit cable is placed in the inspection assembly 1203, FIG. 12A, providing for the detection of changes in the angular alignment of the camera head assembly 100 relative to the push-cable 101 (as in starting a bend in the pipe) an detection of changes in the electro-conductive or ferromagnetic properties around the inspection assembly 1203, such as when encountering an area near a leak in a pipe, or transitioning from plastic to steel or iron pipe. FIG. 12A is a schematic diagram of a pipe mapping system embodiment 1200 illustrating a camera head assembly 100 with an EMF sensor 1202 axially aligned with the push-cable 101 to which a locating signal 1206 has been coupled using a built-in transmitter 1204. FIG. 12B shows the camera head assembly 100 with the cable and EMF sensor unaligned within a leaky bent pipe. For straight sections of piping the cable is approximately coaxial with the inspection camera axis of symmetry and aligned axially at some fixed distance from the inspection camera. Changes in the strength of the cable locating signal 1206 measured at the inspection assembly 1203 occur as a direct result of camera head assembly 100 turns with respect to the cable axis and changes in local ferromagnetic or dielectric properties. This information is useful for localizing a pipe leak 1208 that is injecting fluid (e.g., water) into the soil surrounding the pipe.

In FIG. 12A, an inspection assembly 1203 is shown traversing the interior of a pipe 116 and connected to a push cable 101. The inspection assembly 1203 is equipped with a camera head assembly 100 and an EMF sensor 1202 of an appropriate frequency sensitivity. A built-in transmitter 1204 is connected internally to the push-cable 101 leading into the pipe 116. A predetermined locating signal 1206 is thus coupled onto the push-cable 101 to which EMF sensor 1202 can respond. In FIG. 12A, the inspection assembly 1203 is disposed in a straight segment of pipe 116 so that EMF sensor 1202 and the push-cable 116 are axially aligned. In FIG. 12B, a pair of sensors (not shown) disposed orthogonally to the z-axis of the inspection assembly 1203 can sense changes in relative orientation between the inspection assembly 1203 and the push-cable 101 behind it. In FIG. 12B, the same inspection assembly 1203 is negotiating a bend in the pipe so that the sensor 1202 is no longer axially aligned with the push-cable z-axis. This changes the locating signal 1206 detection at the sensor 1202, which change may be analyzed in processing (not shown) to render some indication on the display (not shown), such as a change in the tracking line, for example. FIG. 12B also shows a leak 1208 in the pipe 116. In this example, such a leak of water or other conductive liquid operates to modify the electro-conductive characteristics of the surrounding soil adjacent to the sensor 1202 and push-cable 101, thereby changing the injected signal 1206 detection at the sensor 1202. By analyzing the character of such a detection change, the processor may alert the operator to the corresponding change in the camera head assembly environment.

Figure 13:
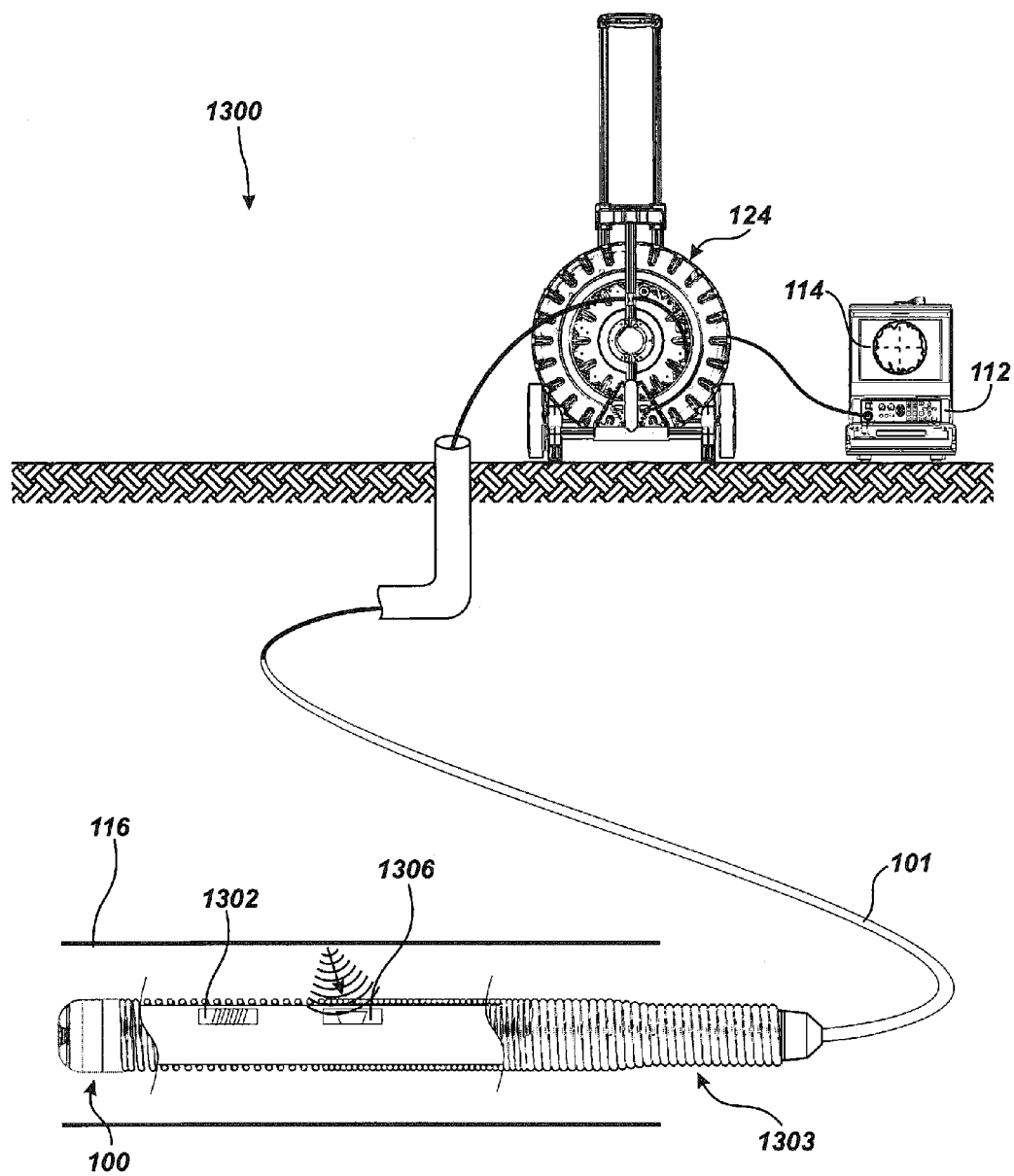
FIG. 13 is a schematic diagram of a pipe mapping system embodiment illustrating a cutaway view of the inspection assembly having an acoustic transducer for producing sonic detection patterns for transfer to a data processing and a display assembly.

FIG. 13 is a schematic diagram of a pipe mapping system embodiment 1300 showing a cutaway view of the inspection assembly 1303 revealing the camera head assembly 100, the EMF sensor 1302 and an acoustic transducer 1306 for producing sonic detection patterns for transfer to a data processor 112 and a display 114. The acoustic transducer 1306 may be mounted inside or outside of the inspection assembly 1303. Acoustic characteristics may be analyzed to estimate the interior pipe surface condition as the inspection camera slides along the pipe 116. Fluid leaks may also be detected and localized by sensing the sounds generated thereby. In FIG. 13, a inspection assembly 1303 is equipped with an acoustic transducer 1306 and is shown traversing the interior of a pipe 116. Signals from the sonic transducer are routed through an ADC (not shown) to digitize the acoustic signals for transfer to processor 112 wherein they are processed to provide information concerning the conditions within the pipe 116, the presence of leaks, etc.

Figure 14A:
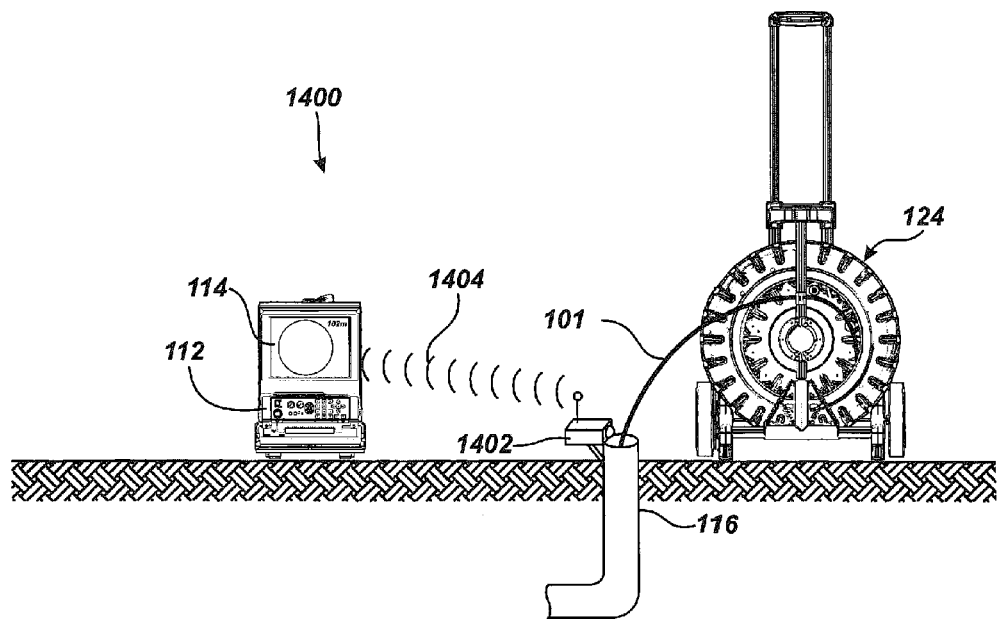
FIG. 14A is a schematic diagram of a pipe mapping system embodiment having a detachable cable-counter embodiment disposed at the entrance of the pipe.

FIG. 14A is a schematic diagram of a pipe mapping system embodiment 1400 having a detachable remote cable-counter embodiment 1402 disposed at the entrance of the pipe 116. Remote cable-counter 1402 is mounted at the cable entry point into the piping system under inspection to improve inspection accuracy by providing a more accurate measurement of cable distance to the camera head assembly. Wireless link 1404 communicates the cable distance measurement data to the data processing system 112 where the data are integrated into the information display 114. The wireless data link 1404 may embody any useful protocol known in the art, such as Zigbee, IEEE 802.15.4, or Bluetooth, for example.

Figure 14B:
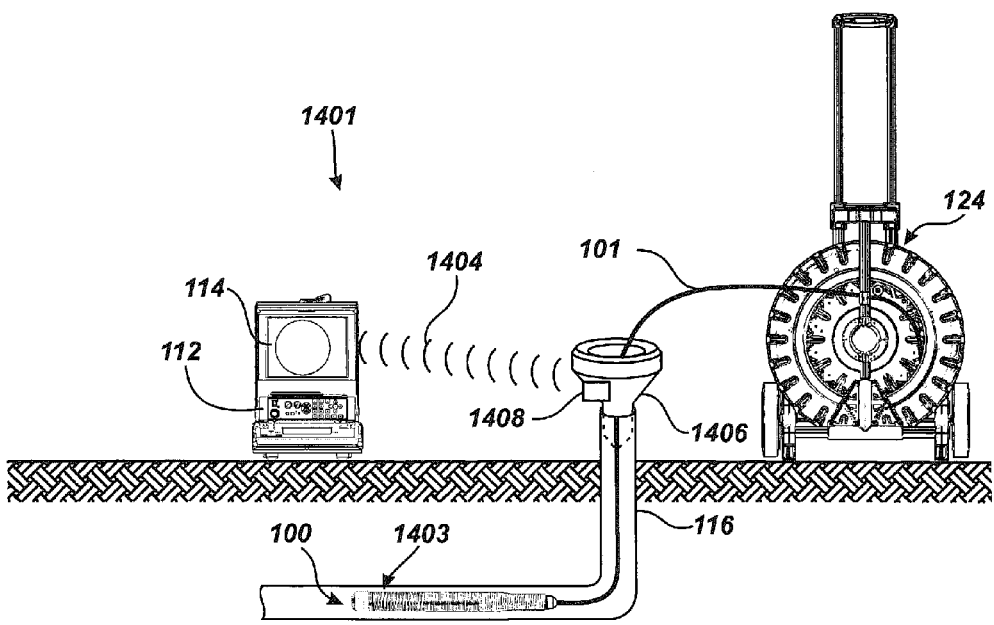
FIG. 14B is a schematic diagram of a pipe mapping system embodiment having a cable-counter embodiment integral to a cable-feed drive mechanism.

FIG. 14B is a schematic diagram of a pipe mapping system embodiment 1401 having a fixed cable-counter embodiment 1408, which is integral to the powered cable-feed drive unit 1406 that is mounted at the entry point to the pipe under inspection during use. A wireless data link 1404 transmits cable distance data to the processing unit 112 where they are combined with data from the inspection assembly 1403 and integrated into the information display 114.

Figure 15:
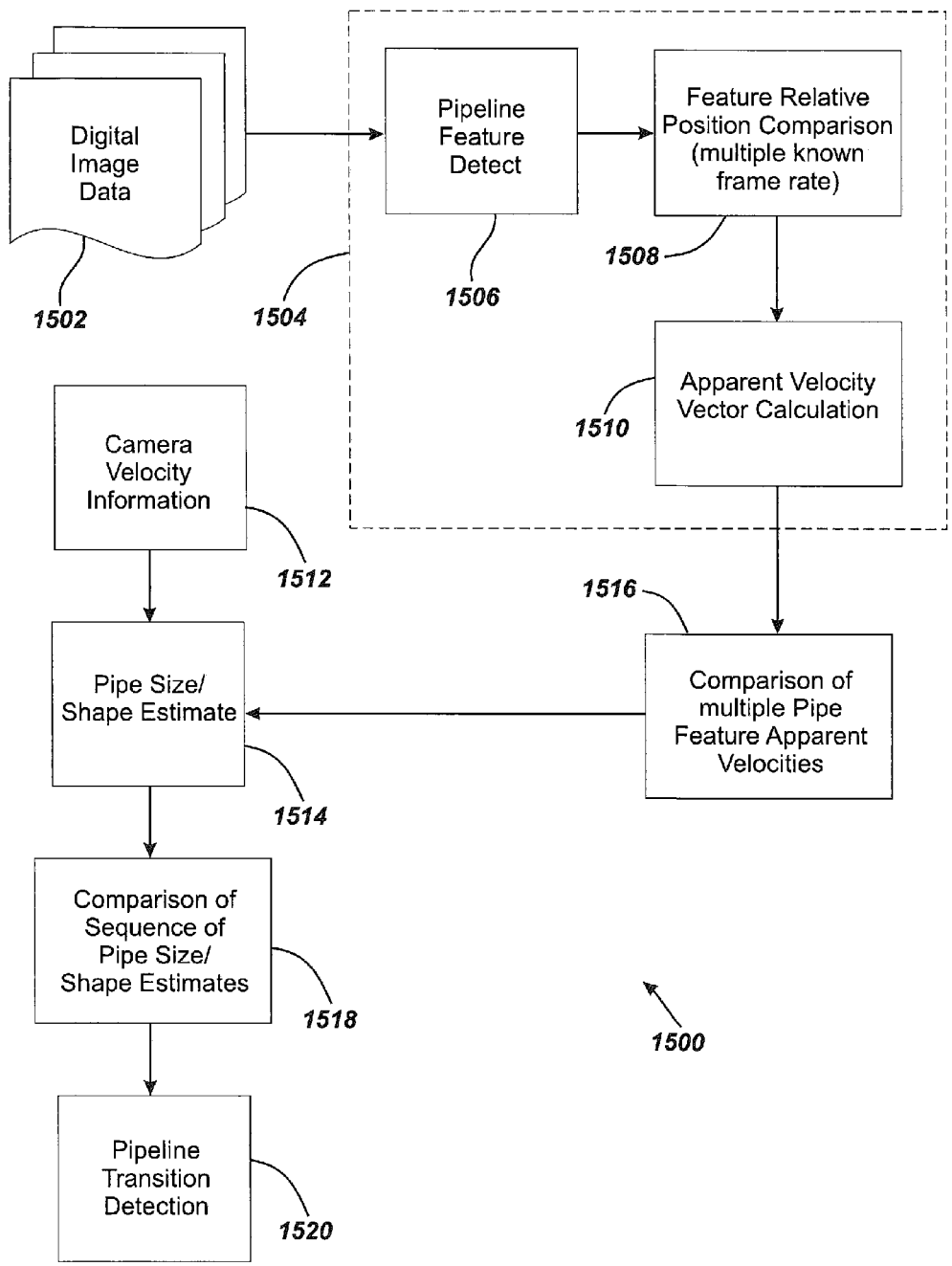
FIG. 15 is a schematic diagram illustrating an embodiment of the processing flow for extracting apparent velocity vector data from digital image data, including apparent velocity data, surface variation data and track and map data.

FIG. 15 is a schematic diagram illustrating a processing flow embodiment 1500 for extracting motion vector data from a single image, including apparent velocity data, surface variation data and track and map data. The size and shape of the inside of the piping system is determined by comparing the apparent velocity and direction of each camera image point to the actual camera velocity measured by the cable-counter and accelerometer sensor. The optical characteristics of the camera lens may be precalibrated to facilitate correction therefor. The inside walls of a larger pipe are generally further from the inspection camera, appearing to move slower than the closer wall of a smaller pipe. Variations from a circular geometry also affect apparent velocity of the inside pipe wall image points. Using these characteristic variations, offset joints, transitions in inside diameter, flattened sections; other pipes joining at Tee's, etc., may be automatically identified and mapped.

In FIG. 15, digitized image data 1502 are analyzed in software to detect pipeline features 1506. The relative positions 1508 of each detected feature over several image frames are analyzed to extract the corresponding apparent velocity vectors 1510. Independently, camera velocity data 1512 are acquired from other local condition sensors and combined with the apparent velocity vectors 1510 to produce a comparison of multiple apparent pipe feature velocities 1516. These feature velocities data 1516 may be used to extract the pipe interior size and shape estimates 1514. The comparisons 1518 of several sequential size and shape estimates are analyzed to produce a pipeline transition detection 1520. Responsive to these results, other calculations may be performed to resolve the pipe interior conditions at the camera head assembly, the direction and distance of camera travel, etc.

Figure 16A:
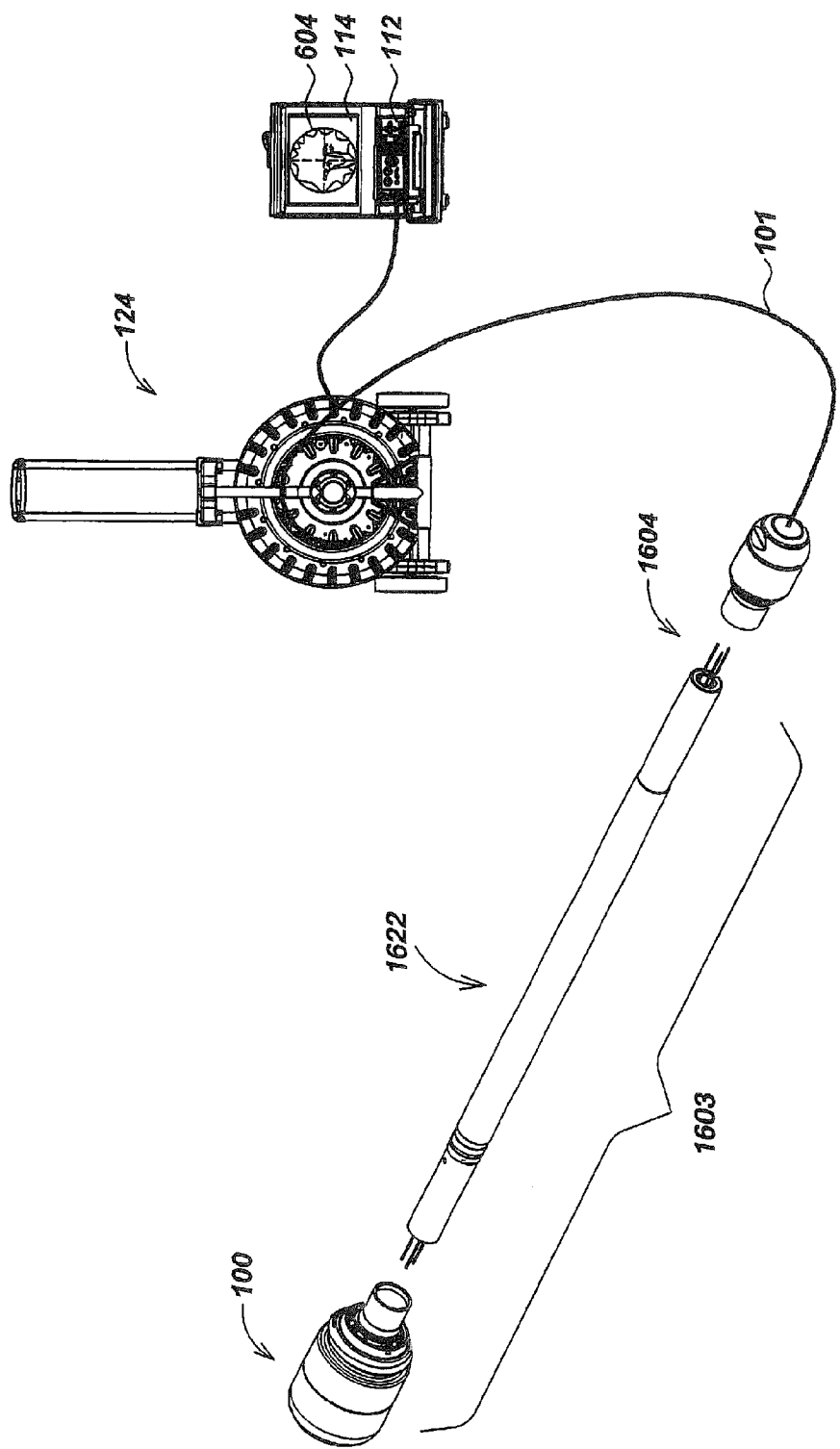
FIG. 16A is an expanded view of a flexible inspection assembly embodiment having an in-line ferromagnetic Sonde embodiment with a central tube for the passage of electrical conductors and/or fiber optic cables.

FIG. 16A is an isometric expanded view of a flexible inspection assembly embodiment 1603 revealing an in-line ferromagnetic Sonde embodiment 1622 having a hollow axial tube (not shown) for the passage of electrical conductors and/or fiber optic cables. The Sonde is actuated by means of a copper winding layer in the cable construction, insulated from the core. In inspection assembly 1603, the camera head assembly 100 also encompasses the accelerometer (not shown) and other local condition sensors (not shown) and is coupled to a cable construction, a portion of which constitutes a ferromagnetic Sonde 1622, and in which a hollow axial tube provides passage for electrical conductors 1604 and fiber-optic cable, for example. The composite camera cable containing electrical conductors 1604 and fiber optic core is coupled by mating plugs to the push cable 101, which then connects to processor 112, which is connected electronically to the display unit 114.

Figure 16B:
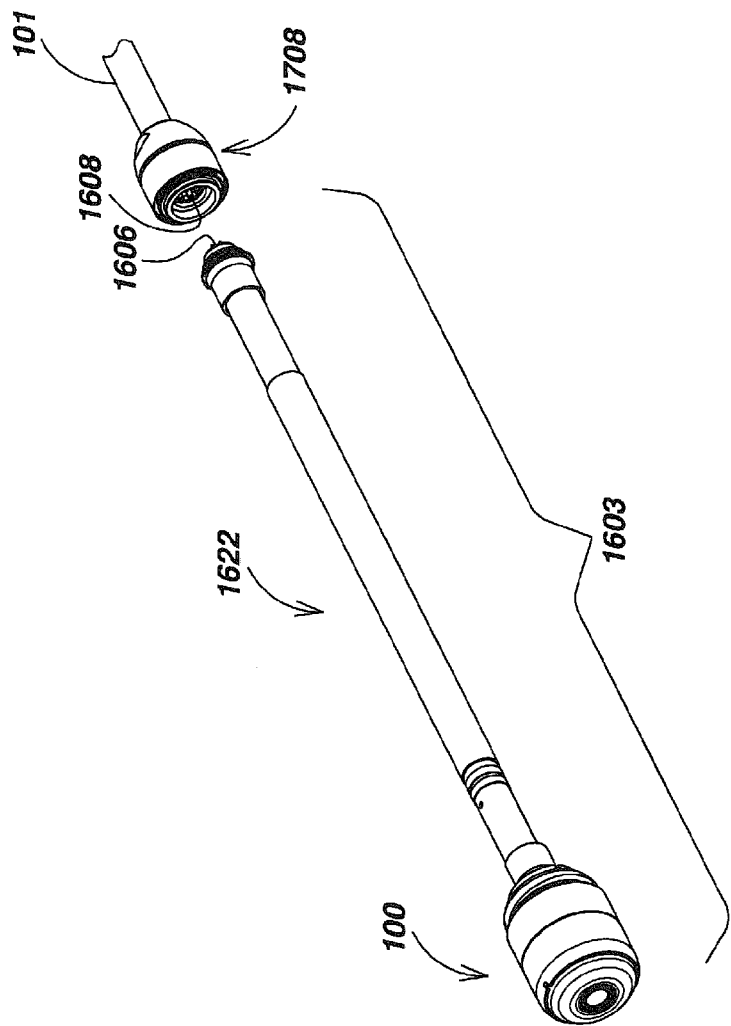
FIG. 16B is another view of the assembly of FIG. 16A revealing the electrical connectors in the push cable.

FIG. 16B illustrates the assembled inspection assembly 1603, including the camera head assembly 100 and integrated Sonde 1622 with electrical connectors 1606, which mate to corresponding connectors 1608 in the push cable 101. A mechanical push-cable termination assembly 1708 is further described below in connection with FIG. 17.

Figure 16C:
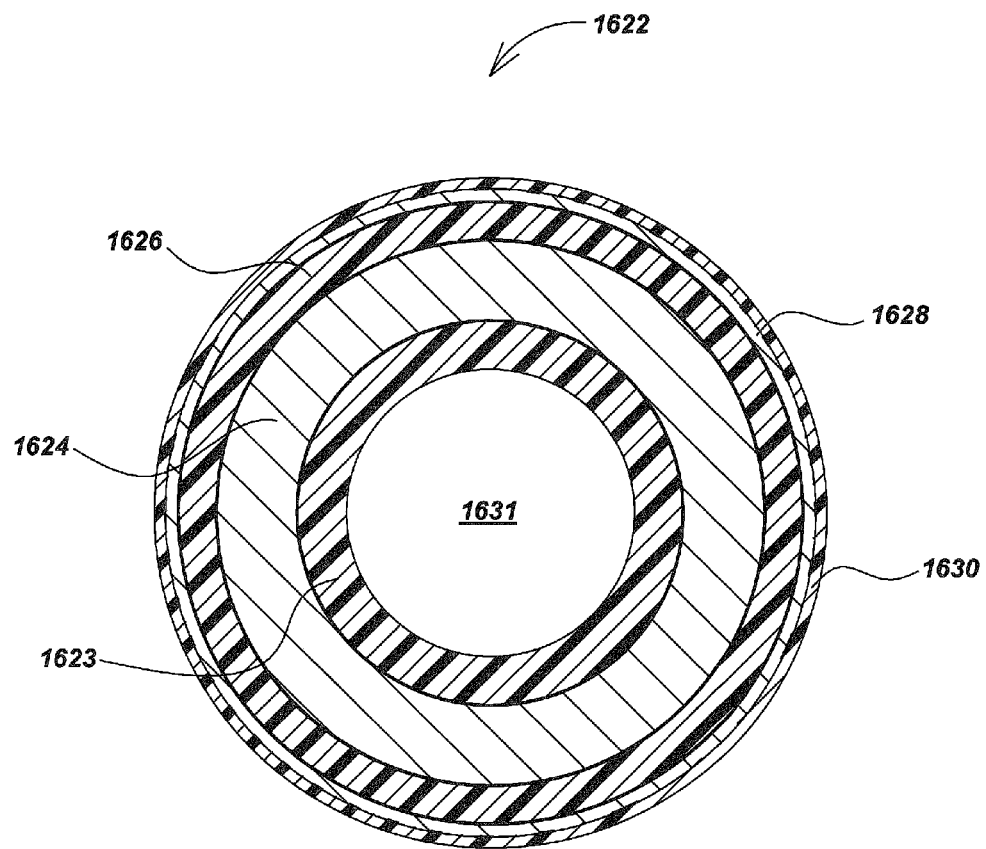
FIG. 16C is a cross-section of the Sonde of FIG. 16A.

FIG. 16C is a cross-section of the integrated Sonde 1622, revealing a flexible semirigid hollow axial tube 1623 that is wrapped with one or more layers of iron wire 1624, which constitutes the ferromagnetic core of the Sonde 1622. The iron wire layer 1624 is covered with an insulating layer 1626 on which is wound a layer of copper wire 1628 constituting the Sonde's coil. The copper winding 1628 is covered with a protective cover layer 1630. The two terminals (not shown) of the copper winding are led through a pin-hole (not shown) into the void 1631 in the axial tube 1623, where they are connected to a power conductor (not shown).

Figure 16D:
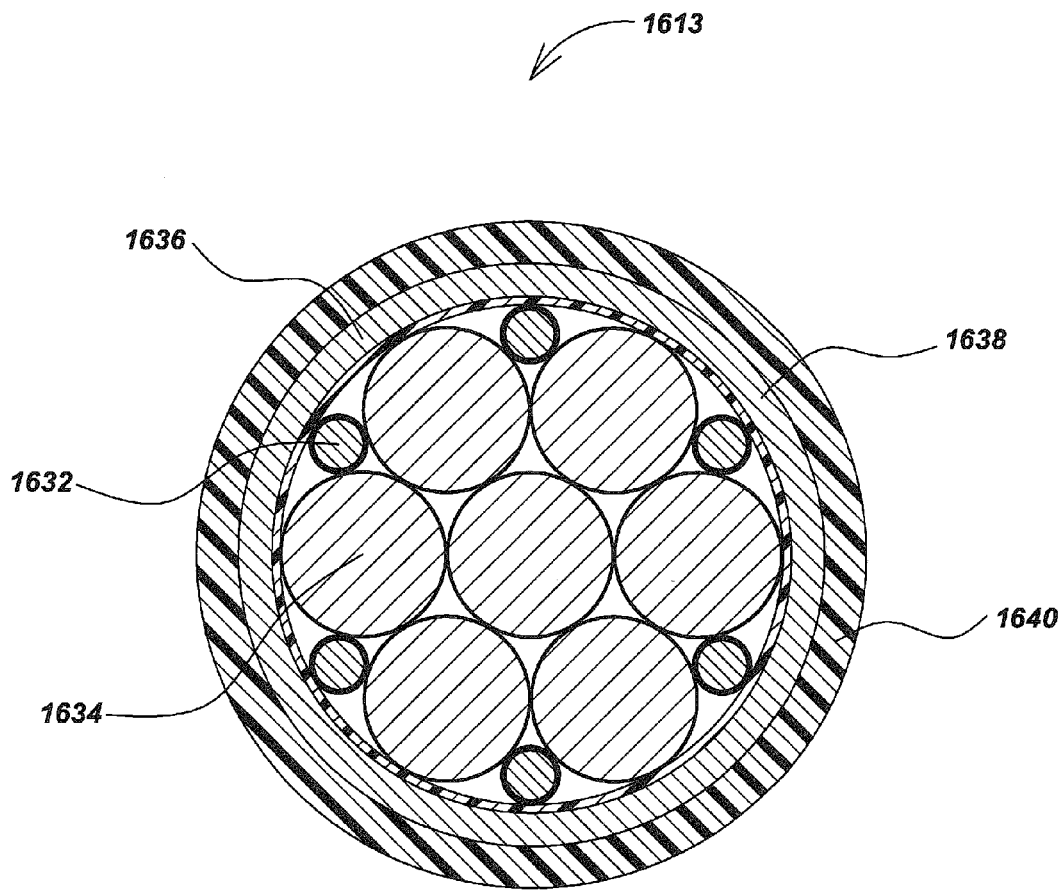
FIG. 16D is a cross-section of an alternate in-line ferromagnetic Sonde embodiment without a central tube.

FIG. 16D is a cross-section of an alternate in-line ferromagnetic Sonde embodiment 1613 without the central tube 1631 (FIG. 16C). With no central void, the through wires are passed between the coils and the core. For example, six copper 28-AWG wires, exemplified by the copper wire 1632, are disposed in the recesses formed by the junction of the circumferences of seven high-permeability core strands, exemplified by the core strand 1634, which may be embodied as insulated high-carbon steel strands, for example. A mechanical filler 1636 wraps about the core construction and a magnet wire coil 1638 wraps around the whole perpendicular to the axis of the cable. A rubber or plastic tube 1640 slips over the whole 1613.

Figure 17:
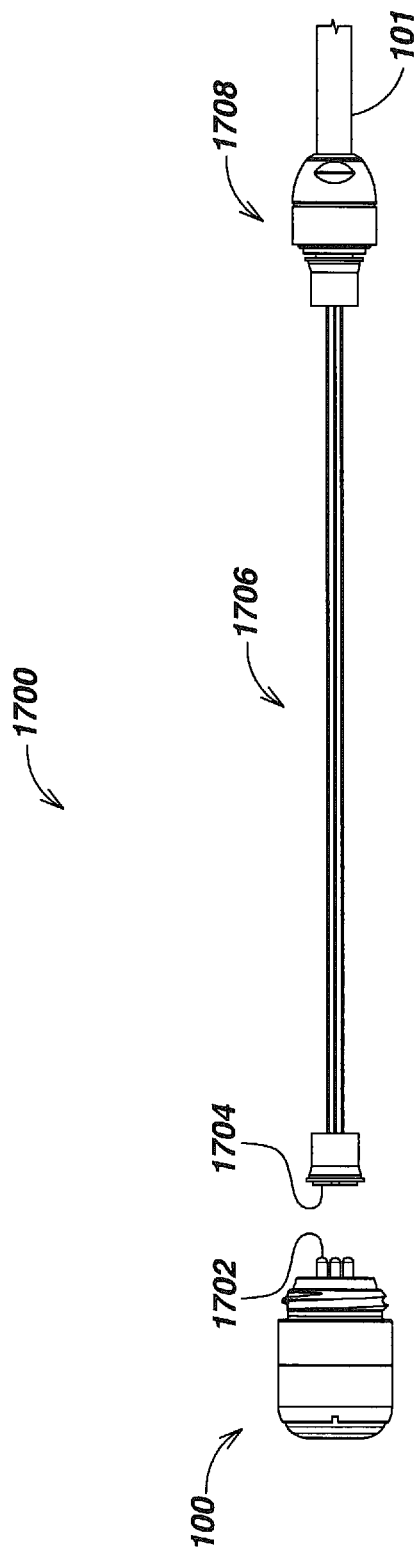
FIG. 17 is another view of the assembly of FIG. 16A revealing the inner camera cable conductors and the electrical connectors to the camera head assembly.

FIG. 17 shows an alternate embodiment 1700 revealing inner camera cable conductors 1706 and the electrical connectors 1702, 1704 to the camera head assembly 100. In assembly, the push-cable outer jacket is removed to expose the inner cable conductors over a distance approximately equal to the distance between the camera head assembly 100 and the mechanical push-cable termination assembly 1708 of the push-cable 101. The resilient composite push-cable core is then trimmed back and mechanically fixed to the push-cable termination assembly 1708. The push-cable conductors 1706 extend forward to an electrical connector 1704, which connects to the back connector 1702 of the camera head assembly 100. FIG. 17 illustrates the camera cable with the outer jacket of the cable removed to expose the inner cable conductors 1706, which terminate in an electrical conductor 1704. The camera head assembly 100 is similarly terminated in a mating electrical connector 1702. This configuration avoids the need for an electrical termination inside the rear spring termination 1708. Alternatively, the pipe mapping system may include an electrical slip ring or an inspection camera push-cable storage drum having two mechanically and electrically separable parts. The direction of separation may be along the axis of rotation of the slip ring, as is taught in U.S. patent application Ser. No. 10/858,628 filed on Jun. 1, 2004 by Mark S. Olsson et al. and entitled "Self-Leveling Camera Head," which is entirely incorporated herein by this reference.

Figure 18A:
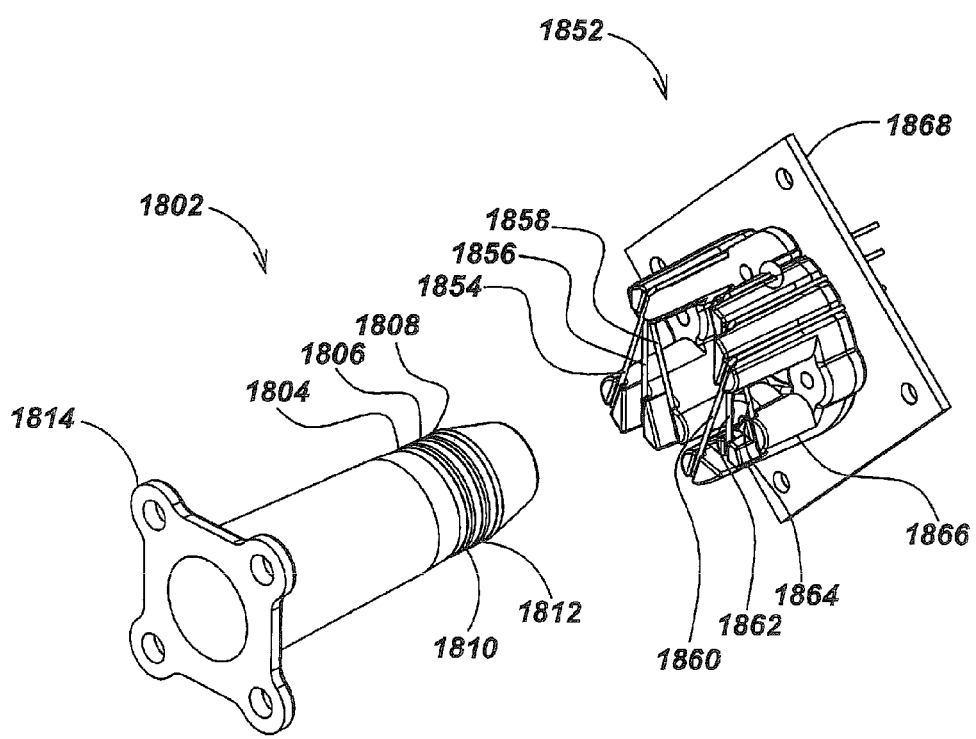
FIG. 18A is an expanded isometric view of a slip-ring embodiment suitable for transmitting electrical power and data signals across a rotating storage drum assembly for the system of FIG. 1.

FIG. 18A is an expanded isometric view of a slip-ring embodiment suitable for transmitting electrical power and data signals across a rotating storage drum assembly 124 (FIG. 1). The direction of separation is along the axis of rotation of the slip ring. A magnet is fixed to one slip-ring part to rotate with respect to the other part to provide an indexing means for measuring the magnitude and direction of slip ring rotation about its axis in support of a cable feed counter. One separable part of the slip ring is mounted on the rotating cable storage drum and the other separable part is mounted onto the rotating cable storage drum support means. The cable storage drum may be removed from its mounting frame if a separable electrical connector is provided therefor. (0109) In FIG. 18A, the plug assembly 1802 is shown on the left and includes a post 1814, a series of contact rings 1804, 1806, 1808 and insulators 1810, 1812 separating the contact rings from one another. The receptacle assembly 1852 includes a mount 1866 and an array of contact pins 1854, 1856, 1858, 1860, 1862, 1864 that are connected to a printed circuit board 1868. When the storage drum is mounted to the frame (124 in FIG. 1), the pins 1854, 1856, 1858, 1860, 1862, 1864 come into contact with the rings 1804, 1806, 1808, thereby connecting the two assemblies electrically to transfer signals from the conductors within the pushrod to devices on the other side of the cable drum, such as the processing unit 112 (FIG. 1).

Figure 18B:
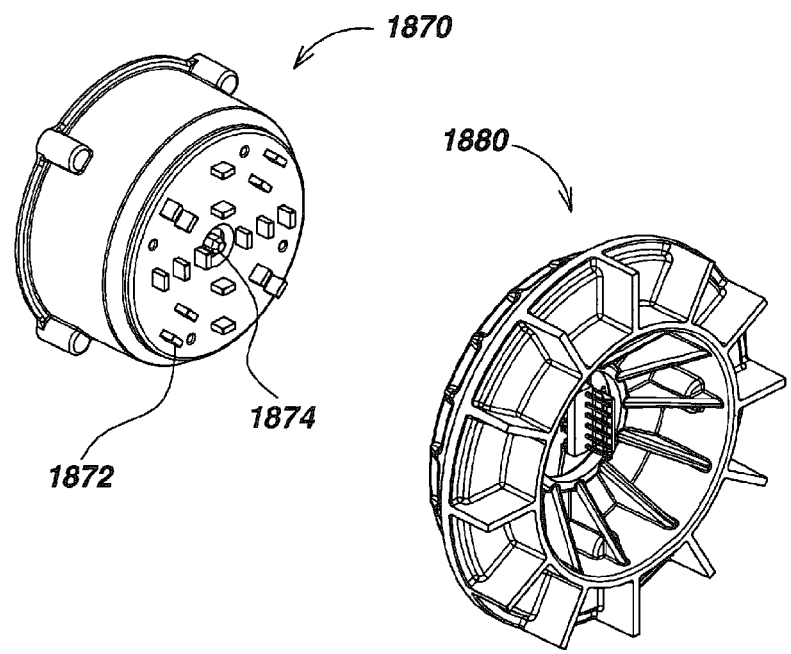
FIG. 18B is an expanded isometric view of an alternate slip-ring embodiment having a "pancake" configuration.
Figure 18C:
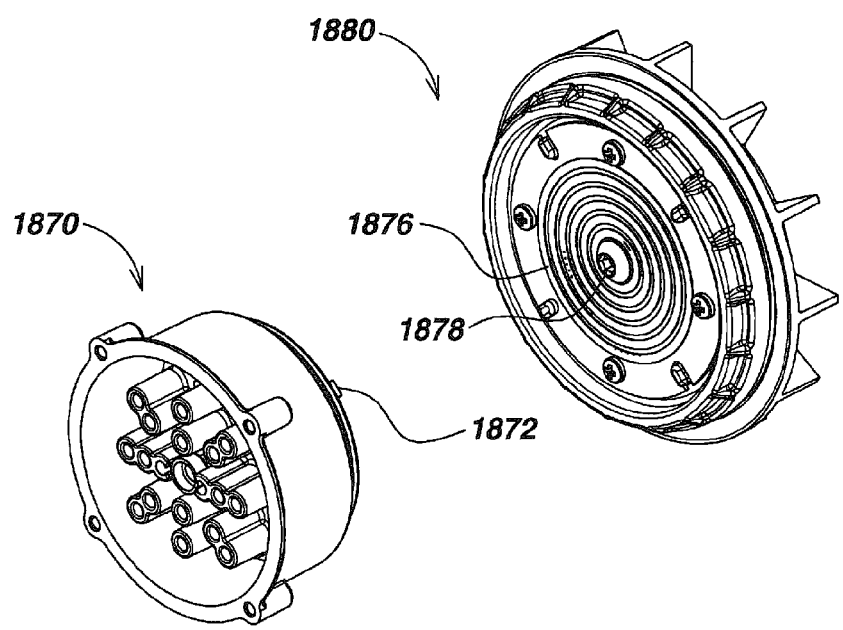
FIG. 18C is another view of the slip-ring of FIG. 18B.

FIG. 18B is an expanded isometric view of an alternate slip-ring embodiment having a "pancake" configuration. The contacts are formed by means of conductive tracks on a flat circular slip-ring "pancake" surface 1880, which electrically connect to corresponding spring-loaded contacts on the opposite slip-ring contacts surface 1870. A series of spring-loaded contacts, exemplified by the contact 1872, are disposed on the flat circular surface 1880 for seating into aligned slots (formed between pairs of conducting rings exemplified by the ring 1876) on the mating contacts surface 1870. A hex-headed male cartridge 1874 is disposed at the center of contacts surface 1870 for mating with a corresponding hex receptacle 1878 on the slip-ring surface 1880, thereby forcing both slip-ring elements 1870, 1880 into alignment upon engagement. The slip-ring surface 1870 also contains an embedded magnet (not shown) that is detected by a fixed Hall sensor (not shown) for indexing rotational movement of the affixed drum with a resolution of one degree or less to provide cable feed length data.

Figure 19A:
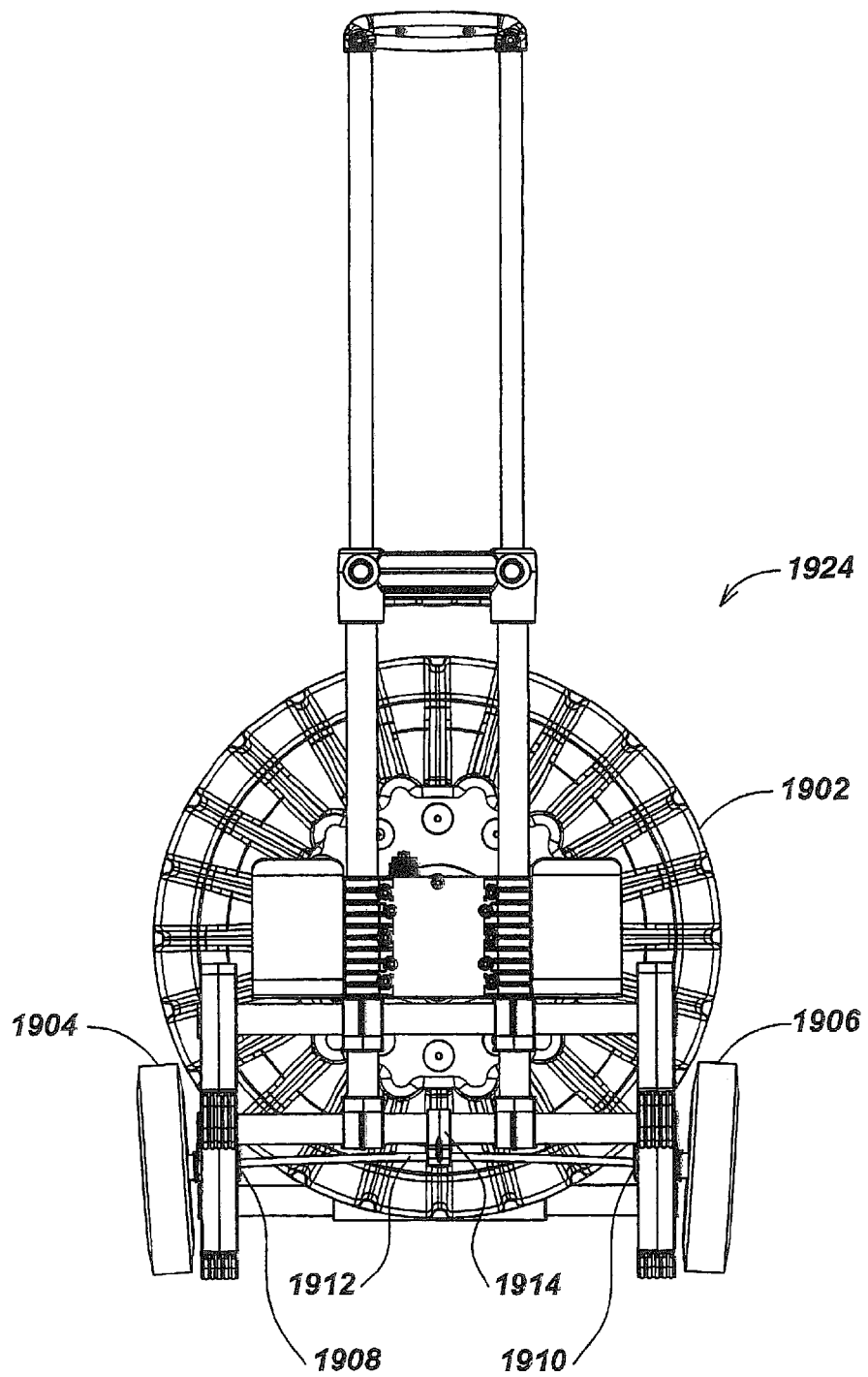
FIG. 19A is a rear view of a push-cable storage drum embodiment showing the frame supported with spring mounts on wheels.
Figure 19B:
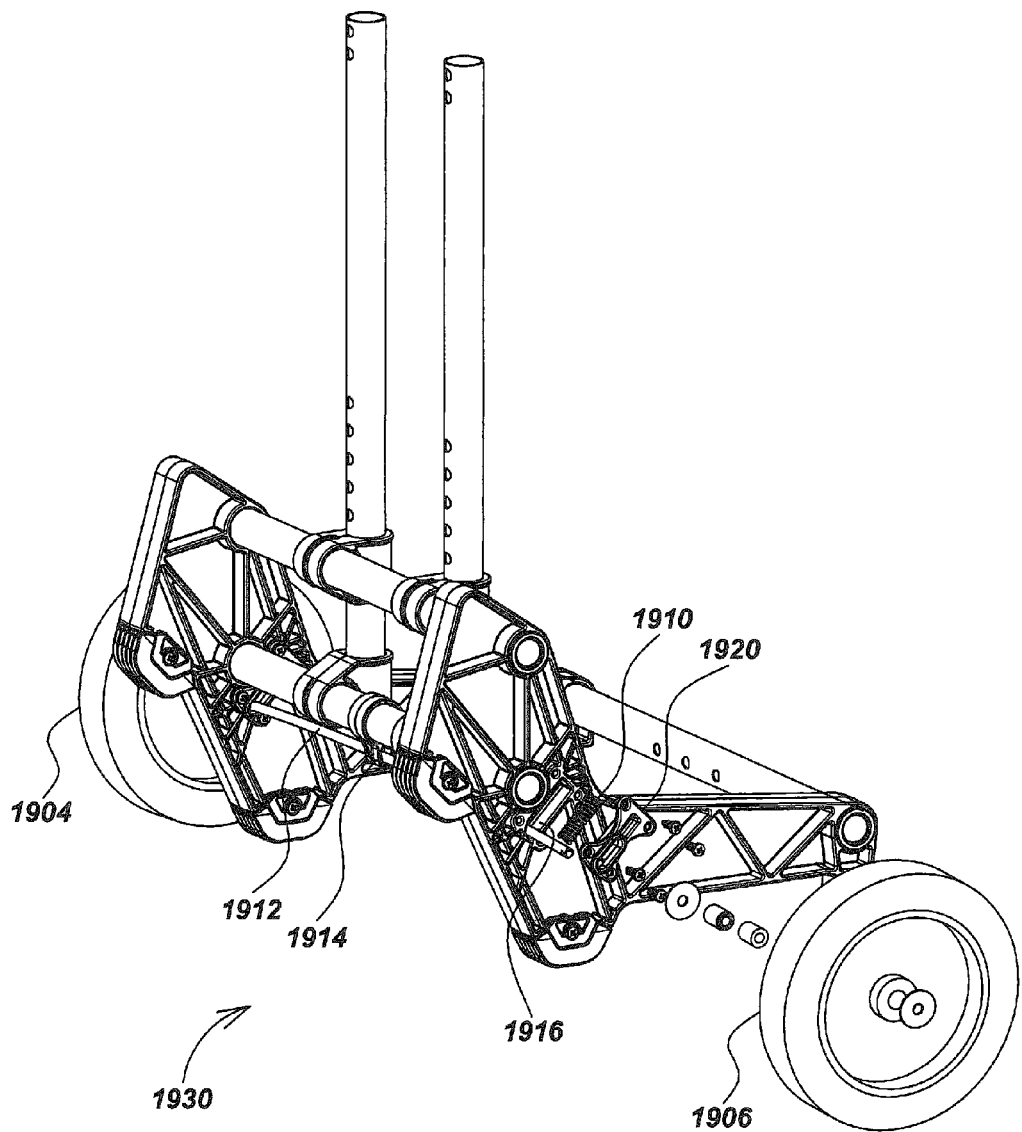
FIG. 19B is a detailed view of wheel, axle and bottom frame embodiments for the push-cable storage drum of FIG. 19A.

Two or more wheels may be mounted onto a push-cable storage drum supporting frame. Also, a telescoping sliding handle may be provided that extends from two support tubes in the push-cable storage drum supporting frame. FIG. 19A is a rear view of a push-cable storage drum embodiment 1924 showing the frame supported with spring mounts on two wheels 1904, 1906, which are mounted using a spring tensioned suspension means. Axle 1912 is partially flexed and constrained by axle flexor 1914 to offset camber in the wheels when under load. This arrangement is simpler and lighter than employing pneumatic tires, for example. Turning to FIG. 19B, a detailed view of the wheels, axle and bottom frame assembly 1930 is shown. In FIG. 19B wheels 1904, 1906, are mounted on an axle 1912 which is partially flexed and constrained by an axle flexor 1914. The dynamic of the flexed axle serves to counteract camber when the wheels are under load. Also, the frame is connected to the axle by springs 1910 inserted into a fabricated slot 1916 and provided with a spring cover 1920, serving to absorb shock while the whole unit is in motion using the wheels.

Figure 20:
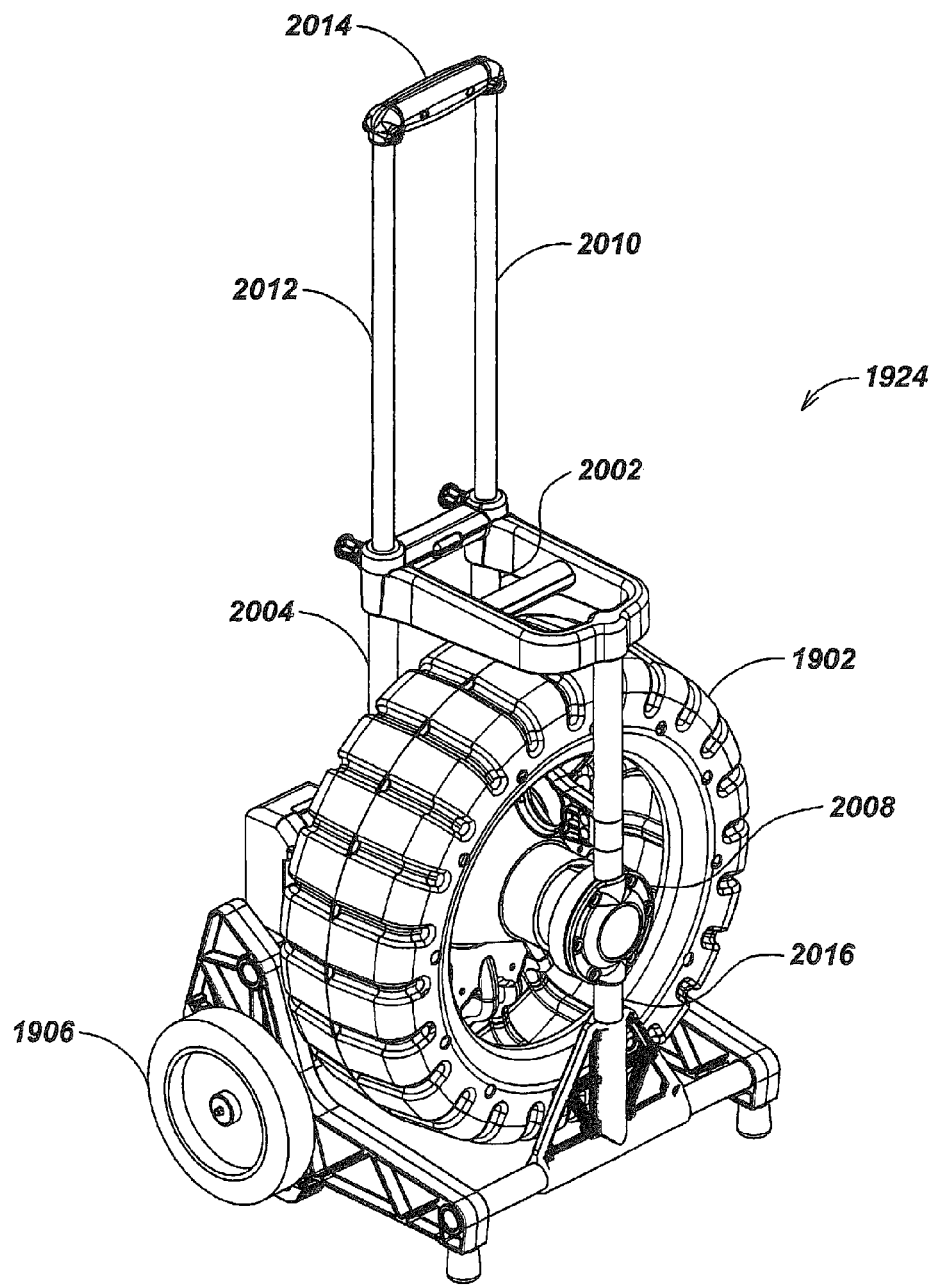
FIG. 20 is a front perspective view of the storage drum of FIG. 19A revealing the handle, frames, support tubes, wheels, drum and rotary hub.

FIG. 20 is a front perspective view of the storage drum assembly 1924 illustrating the handle 2014 inserted into two support tubes 2010, 2012 that form the support for the back side of the storage drum assembly, thereby forming a telescopically extendable handle. An exemplary configuration of the cable drum 1902 and its rotary hub 2008, a single central back support tube 2016, and adjacent molded plastic frame, are also illustrated. The assembly 1924 is provided with two wheels (only wheel 1906 is visible) to facilitate convenient relocation of the storage drum assembly 1924. The drum axis of rotation is perpendicular to the long axis of support tubes 2010 and 2012.

Figure 21:
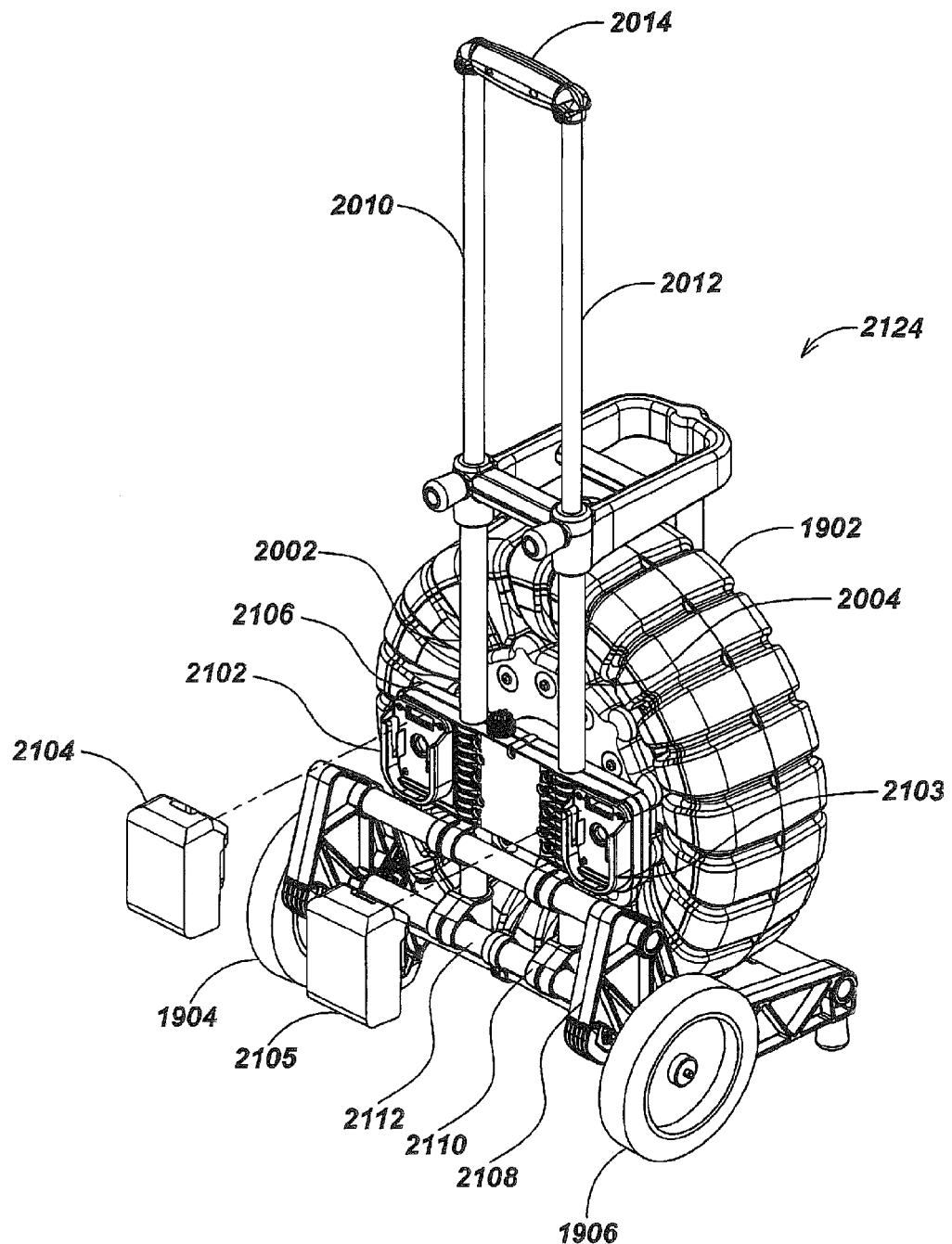
FIG. 21 is a front perspective view of an alternative storage drum embodiment revealing tubes, frame, wheels, battery mounts, and exemplary batteries.

Another configuration of the cable storage drum and support assembly is depicted in FIG. 21. In one embodiment, where one or more support members form the sole support means for one side of a rotating inspection camera cable storage drum supporting means, and further where one or more removable rechargeable batteries may be mounted to the support structure joining said one or more support members to the rotating inspection camera cable storage drum.

Figure 22A:
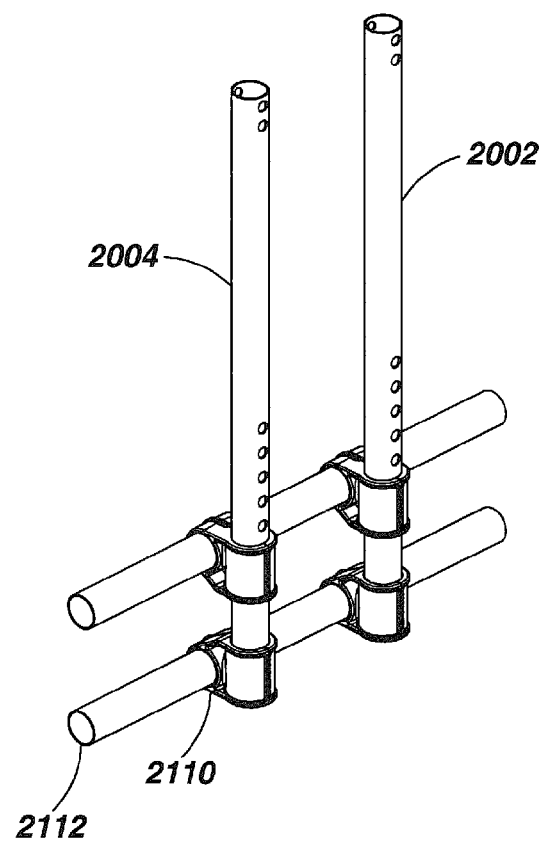
FIG. 22A is a detail view of an exemplary storage drum assembly handle embodiment illustrating the joint between a molded plastic frame member and a support tube.

FIG. 21 is a front perspective view of another storage drum embodiment 2124 revealing the additional battery holders 2102, 2103 mounted, for example, to the molded plastic frame member 2106. Battery holders 2102, 2103 may be mounted at any other useful location in the frame structure. An exemplary rechargeable embodiment of batteries 2104, 2105 is shown. FIG. 21 also shows exemplary embodiments of the handle 2014, handle support tubes 2010 and 2012, frame support tubes 2002 and 2004 and lower molded frame 2108. FIG. 22A is a detail view of an exemplary storage drum assembly handle embodiment illustrating the joint between a molded plastic frame member (e.g., 2110 in FIG. 21) and a support tube (e.g., 2004 in FIG. 21). In this embodiment, a joint is formed by inserting a support tube 2004 into a receiving hollow or hole in a molded plastic frame member 2110.

Figure 22B:
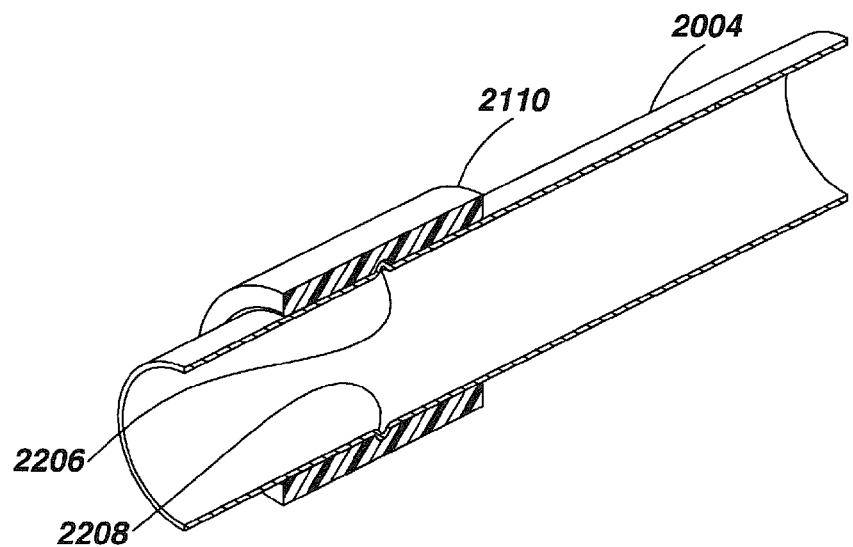
FIG. 22B is a detail view of the joint of FIG. 22A illustrating the disposition of two pressure-expanded dimples for joining the support tube to the plastic frame member.
Figure 22C:
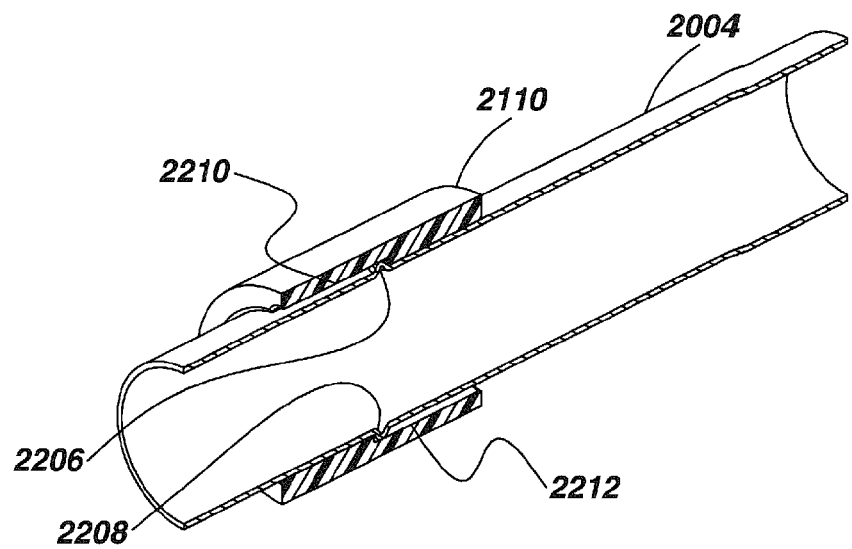
FIG. 22C illustrates an alternative embodiment of the joint of FIG. 22B illustrating the forced seating of the pressure-expanded support tube dimples into a groove molded into the plastic frame member.
Figure 22D:
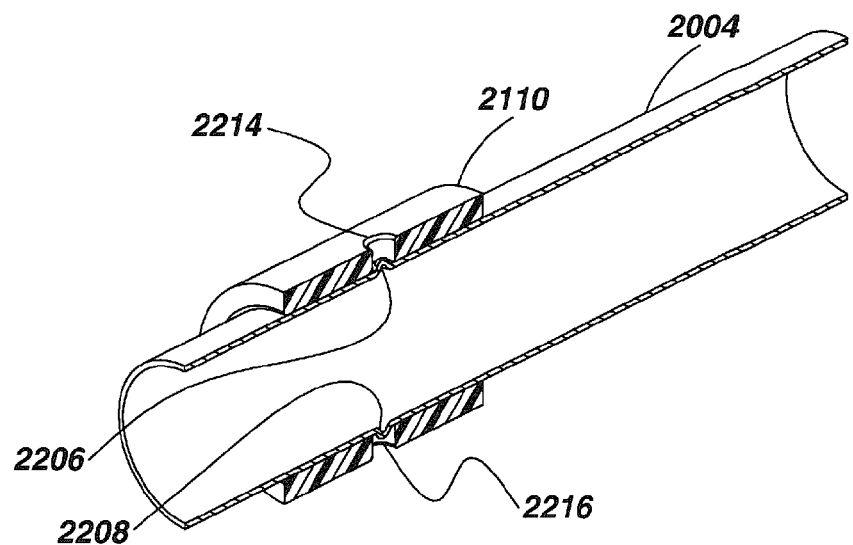
FIG. 22D illustrates an alternative embodiment of the joint of FIG. 22B illustrating the forced seating of the pressure-expanded support tube dimples into matching holes molded into the plastic frame member.

FIG. 22B is a detail view of the joint of FIG. 22A illustrating the disposition of two pressure-expanded dimple elements 2206 and 2208, which are formed in the metal of the tube 2004 using a hydraulically pressurized swaging tool or other means and which fix the tube 2004 into the molded plastic 2110 by expanding a protrusion on either side of the tube as shown. FIGS. 22C and 22D show two variations on the swaging technique. In FIG. 22C, the expanded elements 2206 and 2208 of tube 2004 fit to a groove 2210 formed in the molded plastic component 2110. In FIG. 22D, pre-formed holes 2214 and 2216 are disposed to receive the expanded elements 2206 and 2208.

Figure 23A:
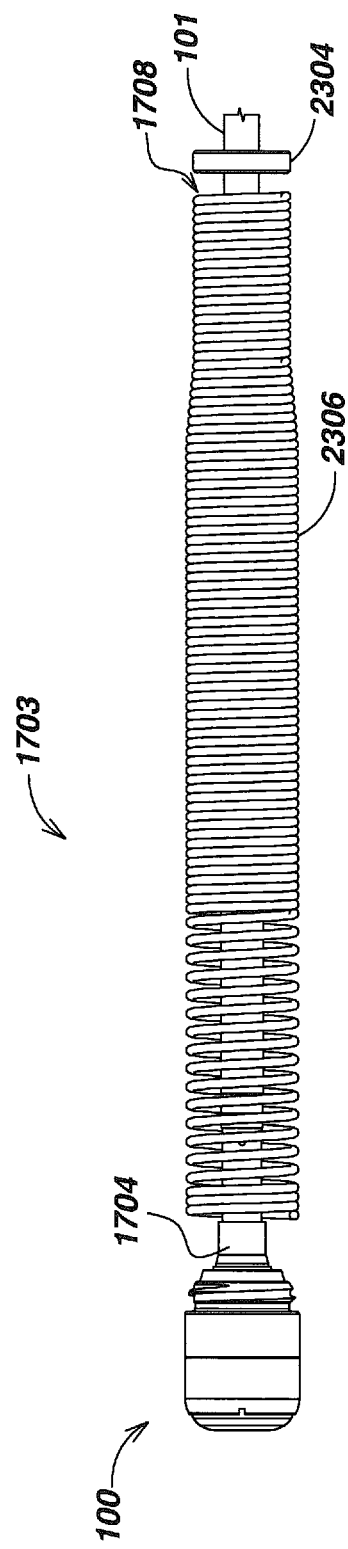
FIG. 23A is a cutaway side view of a partially disassembled inspection assembly embodiment revealing the camera head assembly, the push-cable, the terminating assembly, the locking device, the coil spring, and the internal connectors.
Figure 23B:
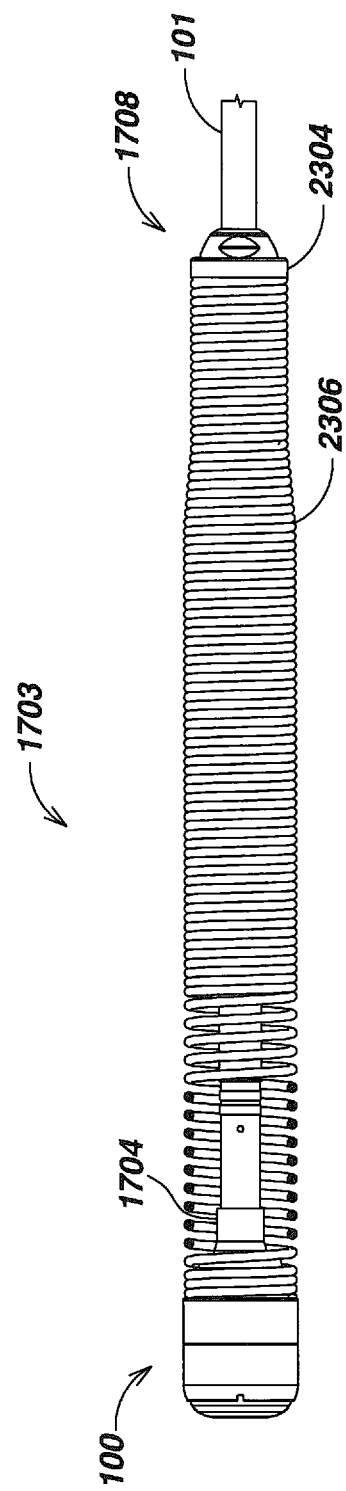
FIG. 23B is a cutaway side view of the fully-assembled inspection assembly of FIG. 23A.

FIG. 23A is a cutaway side view of a partially disassembled inspection assembly embodiment revealing the camera head assembly 100, the push-cable 101, the terminating assembly 1708 (not shown), the locking device 2304, the coil spring 2306, and the internal connectors 1702 (not shown) and 1704. FIG. 23A addresses the construction of a typical inspection assembly and cable with a protective helical spring. The smallest inside diameter of the spring 2306 is larger than the largest outside diameter of the push-cable termination assembly 1708 (with spring locking device removed), allowing the elongate spring 2306 to slide away from the camera head assembly 100 over the push-cable termination assembly 1708 and onto the push-cable 101, thereby exposing the internal connectors 1702 and 1704. After repair or servicing, the elongate spring 2306 slides back over the inspection assembly 1703 and then is secured in place with a spring locking device 2304 that mounts onto the push-cable termination assembly 1708. A termination assembly 1708 at the connecting end of the push-cable holds a spring locking device 2304, which holds the spring in position when put into place during assembly. The tip of the spring wire at the camera-head end of the elongate spring 2306 is received into a matching groove in the camera head assembly 100, thereby locking it at the forward end of inspection assembly 1703. FIG. 23B illustrates the same elongate spring 2306, camera head assembly 100, and push cable 101 in an assembled configuration. In FIG. 23B, elongate spring 2306 is retained by locking device 2304.

Figure 23C:
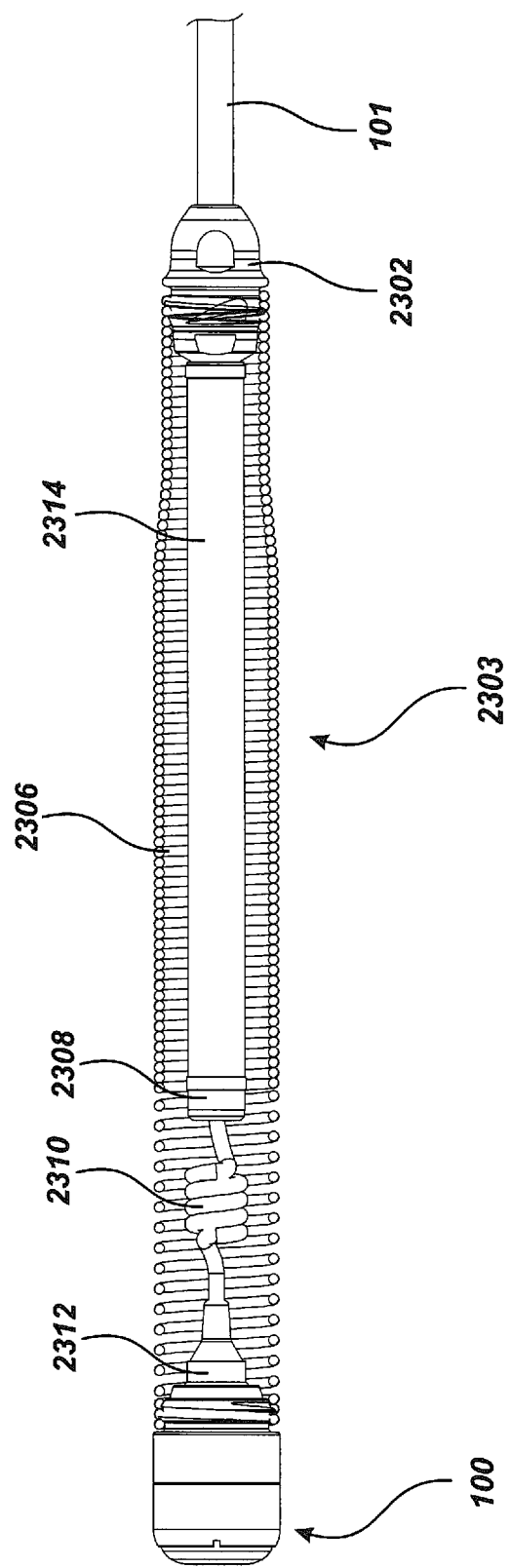
FIG. 23C is a cutaway side view of an alternative embodiment of the fully-assembled inspection assembly of FIG. 23B.

FIG. 23C is a cutaway side view of an alternative fully-assembled camera head assembly embodiment 2303. The push-cable 101 joins to a connector 2302 that also seats the elongate coil spring 2306. Within the coil spring, the in-line Sonde 2314 is electrically connected to connector 2302 at one end and to an attachment means 2308 at the other end. Attachment means 2308 is connected to a coil cord 2310 capable of enough extension to prevent strain from putting the electrical connections at risk of detachment during flexion of the unit. The coil cord 2310 ends in a connector 2312 that joins to the power, data and video pins of the camera head assembly 100.

Figure 24A:
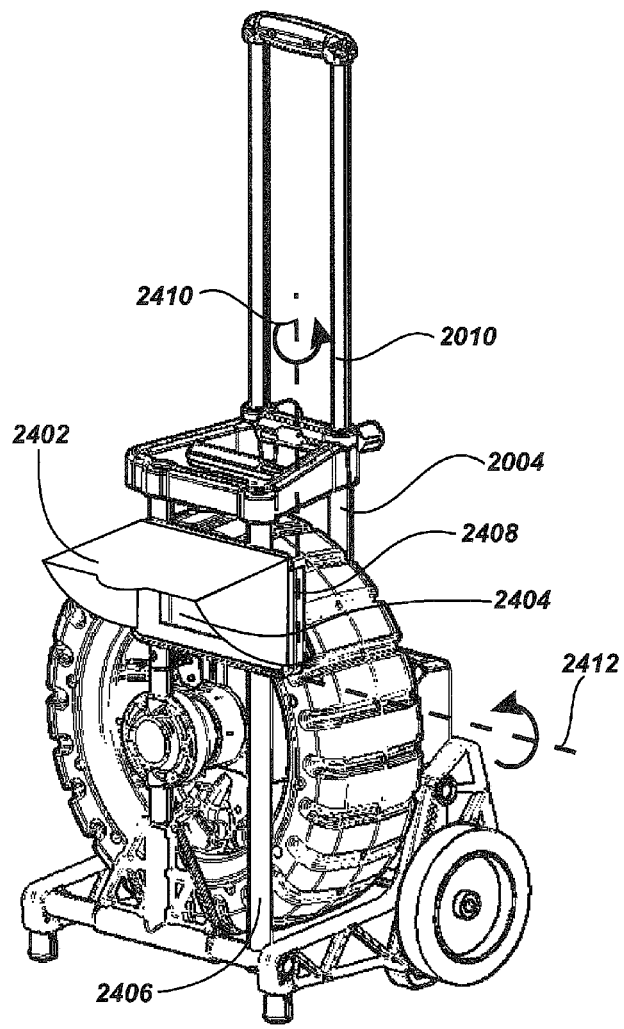
FIG. 24A is a front perspective view of the storage drum of FIG. 19 with an exemplary display monitor embodiment fixed to the storage drum frame and fitted with a hinged sunshade.
Figure 24B:
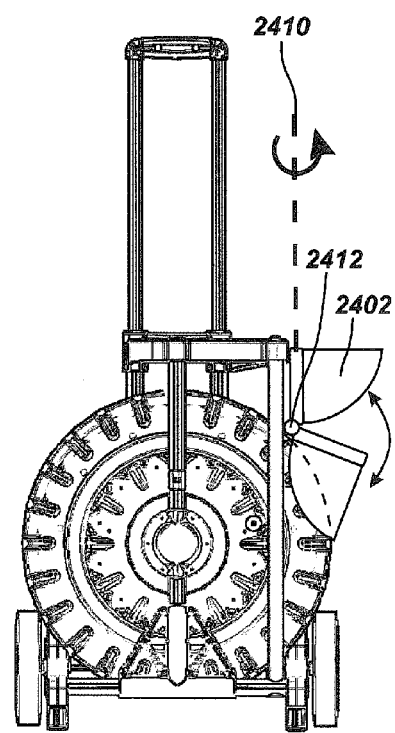
FIG. 24B illustrates the two extreme positions of the hinged sunshade for the monitor of FIG. 24A.
Figure 24C:
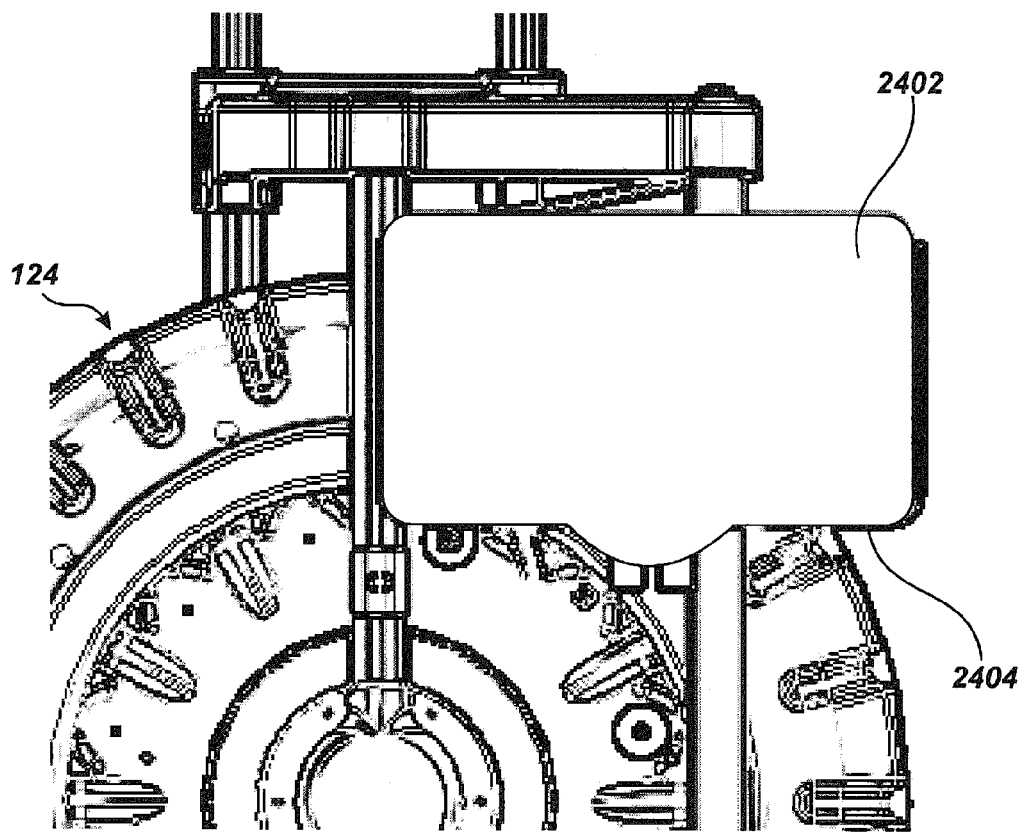
FIG. 24C is a front view of the monitor of FIG. 24A showing the hinged sunshade in the closed position for compact display protection during transit.

FIG. 24A is a front perspective view of the storage drum of FIG. 19 with an exemplary display monitor embodiment fixed to the storage drum frame and fitted with a hinged integral U shaped sun hood. In FIG. 24A the U-shaped sun screen 2402 is shown mounted to the frame member 2406, with a system display unit 2408 mounted onto it in such a manner that the extended hood provides shade to the display screen 2404 improving visibility. FIG. 24B illustrates the hinging action of the sun shade 2402. Horizontal hinge 2412 and vertical hinge 2410 allow positioning of sun hood 2402. FIG. 24C shows an alternate configuration of the sun hood 2402 attached to the cable storage drum support system 124 and folded down for transport in such a way that it protects to the display screen 2404.

Figure 25A:
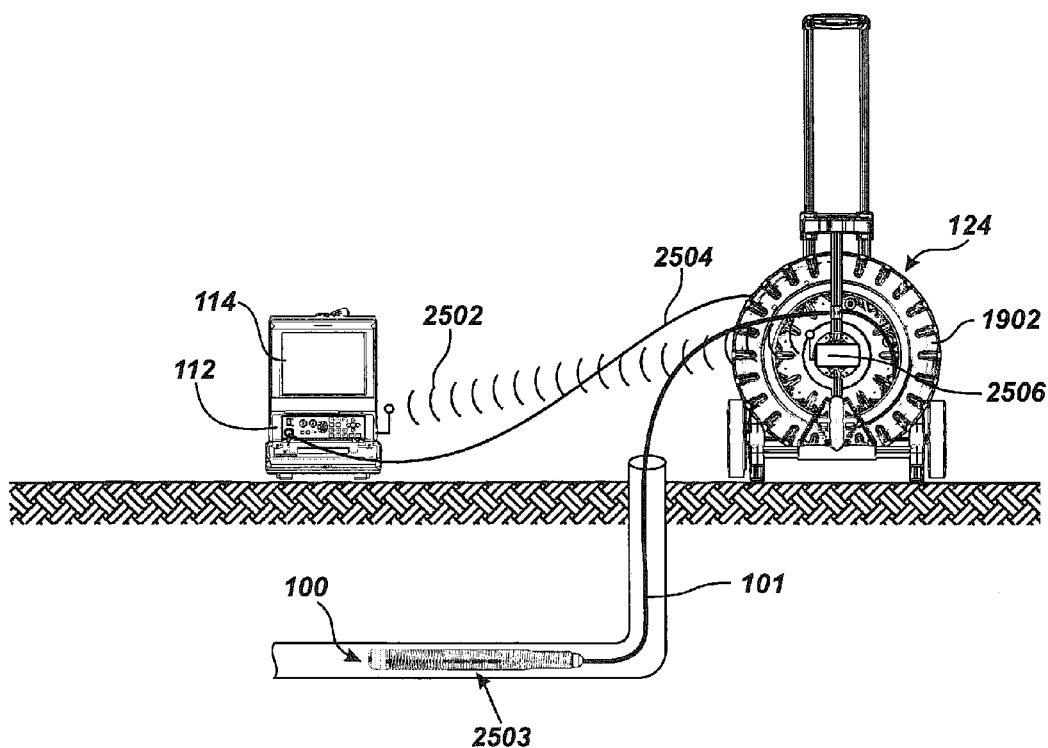
FIG. 25A is a schematic diagram of a cable drum embodiment having an image cable for transferring image data and a wireless transmission unit for transferring local condition sensor data to the processing unit.

FIG. 25A is a schematic diagram of a cable drum embodiment having an image cable for transferring image data and a wireless transmission unit for transferring local condition sensor data to the processing unit; in one embodiment, all or some inspection camera data, except camera image data are transmitted by wireless means from inside the rotating inspection camera cable drum to a separate data processing unit or combined data processing unit and image display means. In FIG. 25A the push-cable 101 containing electrical conductors carries data from the inspection assembly 2503 to the cable storage drum 124. Except for the image data carrier, all the data channels coming from the inspection assembly 2503 terminate at a wireless transmitter 2506 situated, in this example, inside the cable drum assembly 1902. A wireless data link 2502 transmits local condition sensor data and Sonde data to the system data processor 112 while the image data are transmitted to a connector at the data processor 112. The data processing unit 112 integrates image information, local condition sensor data and time tags and assembles the information for display at the display unit 114. Video information may also be transmitted wirelessly as will be shown in FIG. 25B.

Figure 25B:
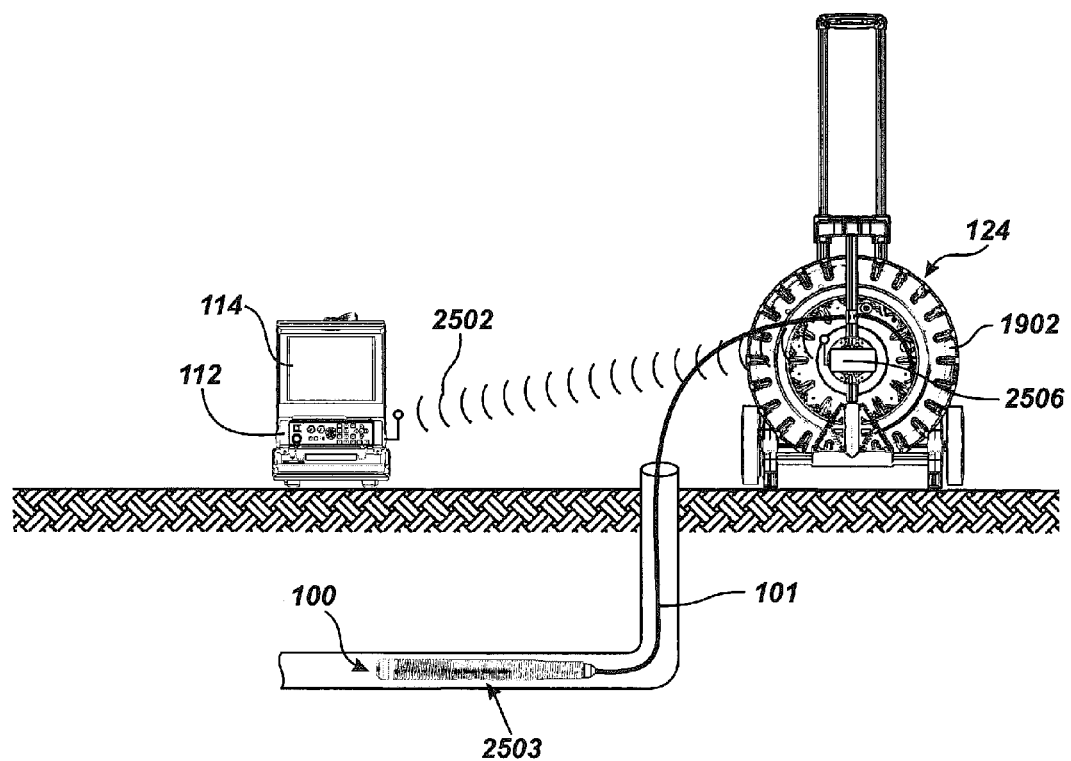
FIG. 25B is an alternate embodiment of the storage drum of FIG. 25A having a wireless transmission unit for transferring all data to the processor.

FIG. 25B is an alternate embodiment of the storage drum of FIG. 25A having a wireless transmission unit for transferring all data to the processor; In this embodiment, all or some inspection camera data, including camera image data are transmitted by wireless means from inside the rotating inspection camera cable drum to a separate data processing unit or combined data processing unit and image display means. In FIG. 25B the wireless transmission unit 2506 transmits all data being carried on the cable 101 from the inspection assembly 2503 including images from the camera head assembly 100. Images may be converted at the cable drum into digital representation from the fiber-optic cable shown in FIG. 7A (710), or they may be converted by circuitry within the camera head assembly 100 or inspection assembly 2503 and transmitted as digital data on an electrical conductor. The cable storage drum support frame may also incorporate a tool receptacle for the storage of wrenches, gloves and other tools commonly needed in locating operations. The cable storage drum may also support a USB interface, for example, for the direct transfer of data to a portable computing device.

Figure 26:
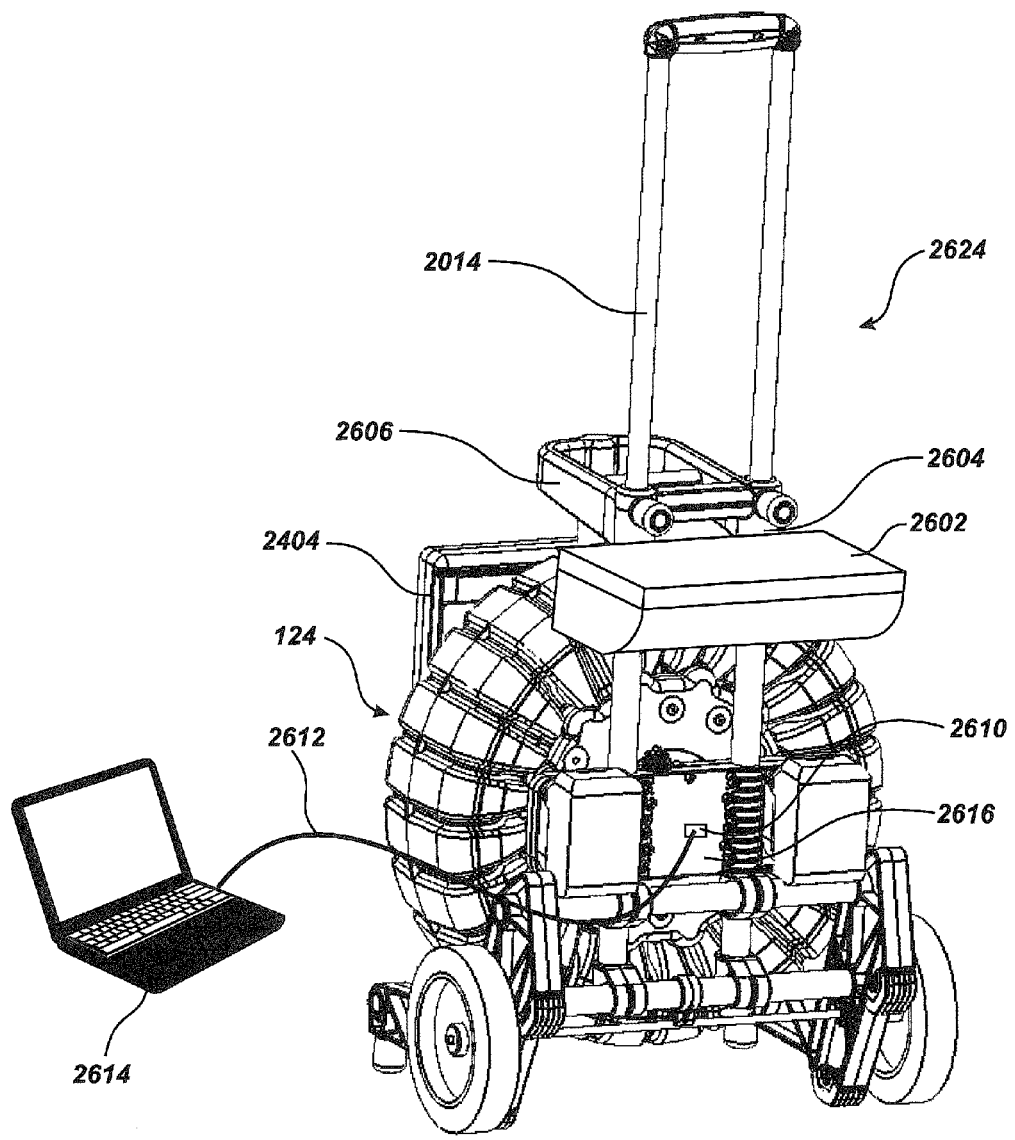
FIG. 26 is a front perspective view of the storage drum of FIG. 19 having a tool tray or box mounted to the back of the cable drum support frame near the handle, having a USB port fixed to the cable-drum support frame for linking to a laptop.

FIG. 26 is a front perspective view of a storage drum embodiment 2624 having a tool tray or box 2602 mounted to the back of the vertical frame support tubes 2604 near the handle 2014 and having a USB data port 2610 fixed to the cable-drum support frame 2616 for linking to a laptop 2614 for exchanging data. The processing and display units of the cable and camera system may be connected wirelessly or by wire to a DVD unit capable of generating DVD recordings of pipe inspection images immediately following an inspection. FIG. 26 shows a tool storage receptacle 2602 mounted directly on the vertical frame support tubes 2604 but storage receptacle 2602 may also be fixed to the upper molded plastic support frame 2606, for example.

A USB data port 2610 is shown integrated into the lower frame assembly on the back. In this example, the USB port 2610 is connected by a USB cable 2612 to a laptop computer 2614 acting as a display unit. The USB port 2610 may be located elsewhere in the frame assembly at any convenient location such as upper molded plastic support frame 2606, for example.

Figure 27:
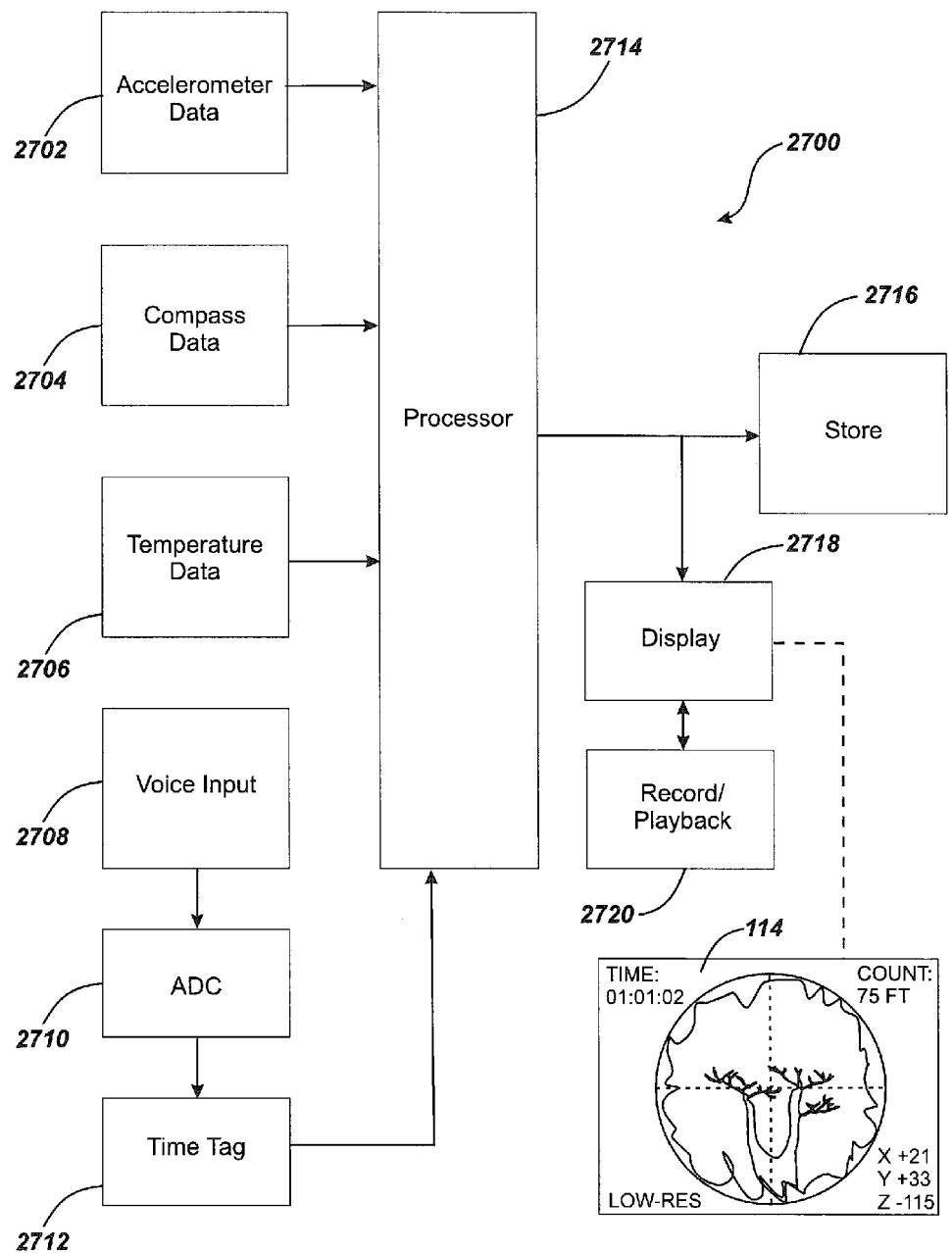
FIG. 27 is a schematic diagram illustrating an embodiment of the processing flow of sensor data packets to the processor and an exemplary display image showing the insertion of sensor data in the margins around a circular image display.

The system of this the disclosure is directed to processing and display units having an interface to a removable media device (such as USB thumb drive or a SD or CF memory card slot) that facilitates recording of camera data, audio, still images and/or videos to the removable media. FIG. 27 is a schematic diagram illustrating a processing embodiment 2700 for transferring inspection assembly sensor data packets to the processor for rendering an exemplary display image showing the insertion of local condition sensor data displays in the margins around a circular image display. The pipe mapping system embodiment may include a voice interface by which user commentary is recorded with time tags correlated to the corresponding image and data store.

In FIG. 27, incoming inspection assembly sensor data include accelerometer data 2702, compass data 2704, temperature sensor data 2706, and an analog voice capture signal 2708, which is transformed to digital voice data by an ADC 2710. These digital voice capture data 2710 are associated with contemporaneous digital time tags 2712 and transferred to a data processing unit 2714. All data packet streams are accepted and coordinated at the data processing unit 2714 for storage in a volatile memory (not shown) from where they may be transferred under program control to a permanent data store 2716 for possible storage and to the display 2718 for possible display to an operator and presentation to the DVDR unit 2720 for recording under operator control, for example. In the display 2718, key data may be rendered as images for insertion in the margins around the central circular image display 114, for example. These graphical formats may be user-configurable through software configuration.

Figure 28:
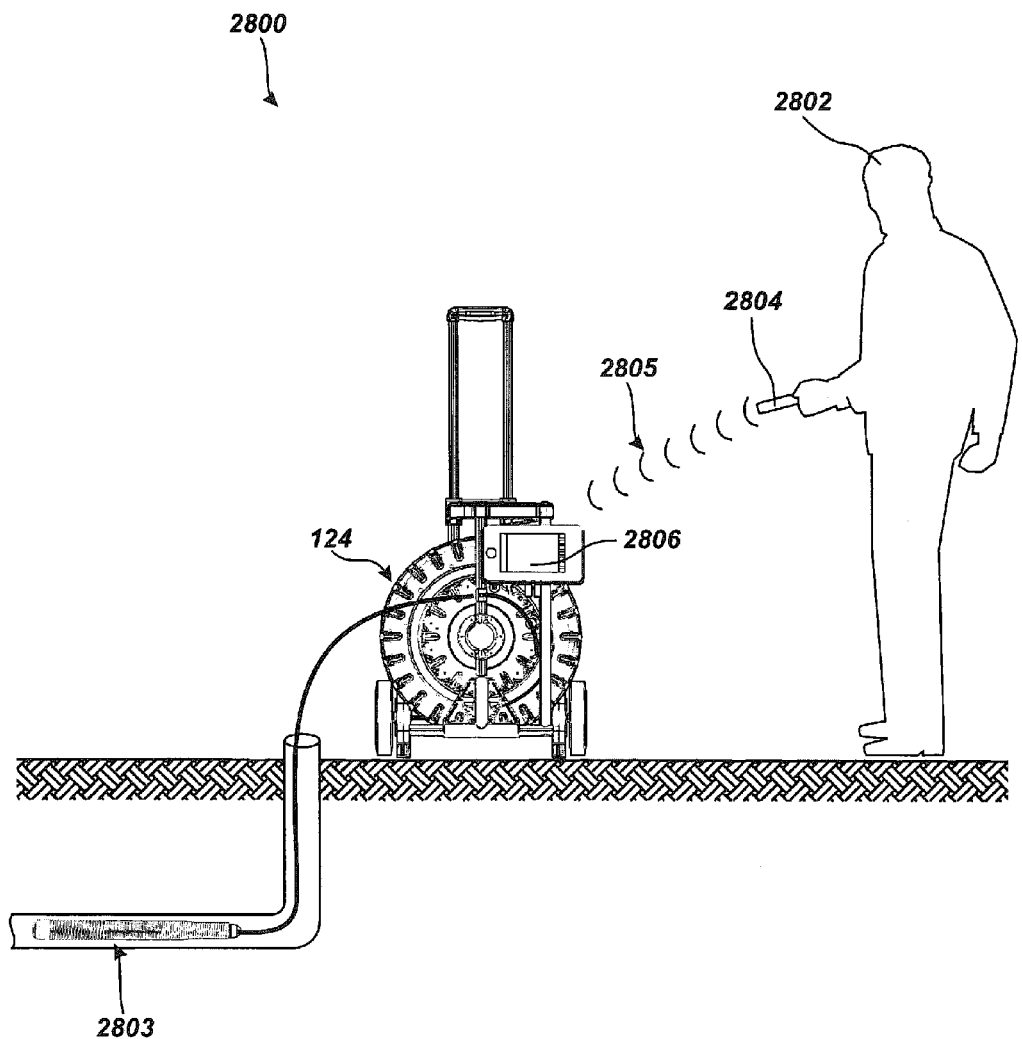
FIG. 28 is a schematic diagram of a pipe mapping system embodiment illustrating the use by an operator of a wireless remote control to record a wirelessly sent voice notation or to send commands to the camera unit or other system elements by way of the processor.

The pipe mapping system of this the disclosure may include a voice interface by which user commentary is recorded with time tags correlated to the corresponding image and data store. A durable wireless controller may be provided to facilitate remote operator control of elements in the push-cable storage drum and inspection assemblies, such as camera head assembly, cable drum motor, voice signal recording and other manually-controllable system elements, or example. FIG. 28 is a schematic diagram of a pipe mapping system embodiment 2800 illustrating the use by an operator 2802 of a wireless remote control transmitter 2804 to transmit a wireless signal 2805 incorporating, for example, a voice signal for recording or various control commands to the camera head assembly or other manually-controllable system elements by way of the processor 2808 (not shown). In one embodiment, the pipe mapping system includes a durable remote control transmitter facilitating operator control of various system functions. In FIG. 28 a scenario is depicted illustrating this embodiment, in which an operator 2802 is equipped with a remote control device 2804 while operating the pipe inspection system. The display 2806 is mounted on the frame of the cable storage drum assembly 124 and is integrally attached to a processor unit 2808. The remote control transmitter 2804 may be operated to control voice and image recording, cable drive motor operation, and display configuration options, for example.

Figure 29A:
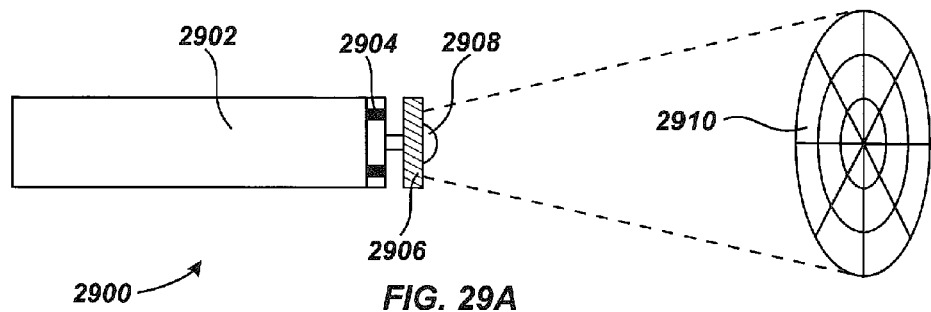
FIGS. 29A-C are schematic diagrams illustrating structured-light techniques adapted for use in a laser-driven pipe inspection camera lighting unit.
Figure 29B:
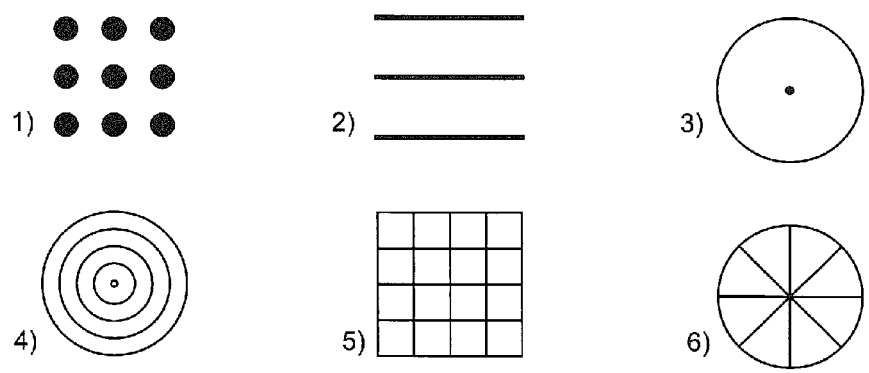
Figure 29C:
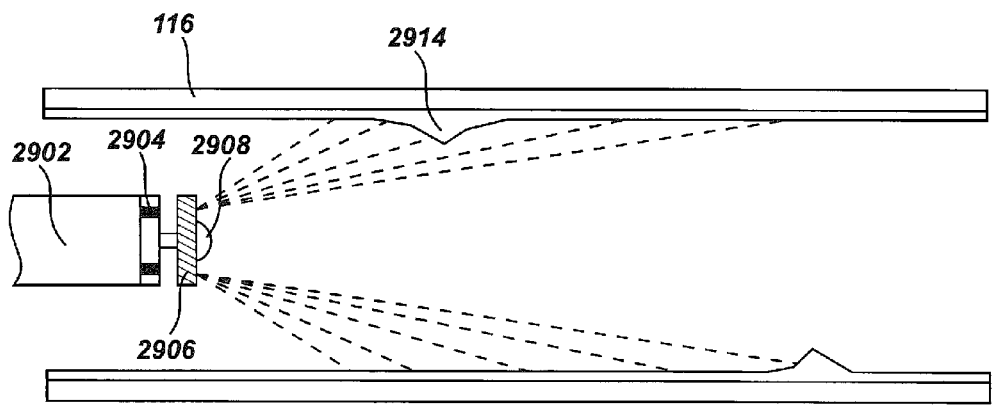

Another pipe mapping system embodiment includes one or more diode lasers and an associated diffraction grating or holographic element assembly for use as a source of structured light illumination for the video camera, thereby facilitating acquisition of dimensional information suitable for establishing the 3D character of the interior of the pipe under inspection. FIGS. 29A-C are schematic diagrams illustrating a structured-light techniques adapted for use in a laser-driven pipe inspection camera lighting unit of this disclosure. At least one diode laser emitter is provided as the camera-head light source, coupled with a pattern projection means such as a diffractive film or grating or a holographic element to create a structured light pattern within the pipe whose reflections may be used to develop 3D mapping of the pipe interior using any useful technique known in the art.

In FIG. 29A the structured lighting assembly 2900 is shown fixed to the camera head assembly 2902 and includes two diode laser light sources, exemplified by the diode laser source 2904, but any useful number of these sources may be included. Laser light from source 2904 is directed through a diffraction grating 2906 causing the projection of a structured light pattern 2910 within the pipe. An imaging detector 2908 senses the reflection of laser light from the interior pipe surfaces on which the pattern falls. These image data are combined in the processor (112 in FIG. 1) with other information such as, for example, camera head assembly orientation, location and rate of movement relative to the pipe interior. This additional information facilitates operation of the structured light system 2900 as a dynamic optical ranger. Emission of the predefined image pattern provides a basis for recovering the distortion of the reflected pattern for use in characterizing the surface irregularities within the pipe under inspection by producing a point by point analysis of the two digitized images (sent and returned).

FIG. 29B illustrates several transmitted image patterns useful for the structured light method of this disclosure. Clearly, any practitioner skilled in the art can appreciate that a more complex pattern facilitates more detailed reconstruction of the pipe interior.

FIG. 29C illustrates a camera head assembly 2902 equipped with a structural lighting assembly disposed inside a pipe 116 under inspection. Two laser emitters 2904 are disposed behind a diffraction grating 2906 to produce a structured light pattern directed along the broken lines to illuminate a region of the pipe interior within the FOV of image detector 2908, including a surface irregularity 2914. The detector 2908 captures FOV images of the light reflected from the inner pipe surface and the processor (not shown) compares these FOV image data with the predetermined structured light pattern to produce Cartesian range data at a predetermined image frame rate. These reflective changes in pattern received at the camera detector 2908 provide the basis for calculating pipe wall surface characteristics in the system data processing module, which then facilitate the rendering of a 3D image of the interior pipe surfaces when location and orientation data from other inspection assembly local condition sensors are processed to resolve camera head assembly movement and orientation. This system may usefully employ a visualization subsystem for acquiring a voxel array filled with red, green and blue (R, G, B) image detector output values at X, Y and Z locations using a registration technique such as the Fast Landmark Graph (De Piro, CalPoly) method to isolate subgraph isomorphisms, or similar method, for example.

Clearly, other embodiments and modifications of this disclosure may occur readily to those of ordinary skill in the art in view of these teachings. Therefore, the presently claimed invention is to be limited only by the following claims and their equivalents, which include all such embodiments and modifications when viewed in conjunction with the above specification and accompanying drawings.

We claim:

1. A system for mapping pipes under inspection, comprising:
   a push-cable;
   a sonde coupled to the push-cable, the sonde configured to be inserted into a pipe during inspection;
   a locator configured to receive signals from the sonde and generate position information associated with the pipe from the received sonde signals;
   a processing element configured to receive the position information from the utility locator and generate mapping information associated with the pipe; and
   a non-transitory memory for storing the generated mapping information.

2. The system of claim 1, wherein the locator includes a GPS receiver.

3. The system of claim 2, wherein the GPS receiver is configured to receive locating data and compare the data to stored map data.

4. The system of claim 2, wherein the stored mapping information includes data provided from the GPS receiver.

5. The system of claim 1, wherein the locator is an omni-directional locator.

6. The system of claim 1, further comprising a camera head coupled to the push-cable, wherein the processing element receives image or video data from the camera head and associates the mapping information with the image or video data, and wherein the image or video data is stored in the non-transitory memory.

7. The system of claim 1, further comprising rendering the mapping information on a user display.

8. The system of claim 6, further comprising one or more local condition sensors disposed in the camera head.

9. The system of claim 8, wherein the mapping information is generated in part based on data received from the one or more local condition sensors.

10. The system of claim 6, further comprising a light source disposed on the camera head to project light on the pipe being inspected.

11. The system of claim 10, wherein the processing element is further configured to generate a GUI image data signal representing a three-dimensional (3D) map of the interior surface of the pipe under inspection responsive to differences between the image sensor data signal and the light projected on the pipe being inspected.

12. The system of claim 10, further comprising:
one or more local condition sensors, wherein each local condition sensor includes an output for producing a corresponding sensor data signal;
an input of the processing element for receiving a local condition sensor data signal; and
an output of the processing element for producing a GUI data signal representing conditions in the pipe under inspection.

13. The system of claim 12, wherein the local condition sensor comprises a three-axis accelerometer.

14. The system of claim 12, wherein the local condition sensor comprises a three-axis compass sensor.

15. The system of claim 12, wherein the local condition sensor comprises a gyroscopic sensor.

16. The system of claim 12, wherein the local condition sensor comprises a temperature sensor.

17. The system of claim 1, further comprising a cable-counter for providing cable deployment information to the processing element.

18. The system of claim 12, further comprising a three-axis accelerometer and/or a three axis gyroscopic sensor, wherein the image or video data is rotated responsive to an output of the three-axis accelerometer and/or three axis gyroscopic sensor for display or for storage in a memory.

19. A pipe inspection system for mapping a pipe under inspection, the system comprising:
a camera head assembly including an image sensor having a field of view (FOV) and an output for producing an image sensor data signal representing a (FOV) image;
a semi-rigid push-cable assembly coupled to the camera head assembly for urging the camera head assembly along the interior of the pipe under test;
a processor including:
programming for comparing a plurality of (FOV) images to detect and extract image feature data representing features of the inner surface of the pipe under inspection;
programming for producing apparent velocity data representing the apparent velocity of one or more inner pipe surface features with respect to the image sensor (FOV) responsive to the image feature data; and
programming for producing a GUI image data signal representing a three-dimensional (3D) map of the pipe under inspection responsive to the apparent velocity data; and
a display coupled to the processor for displaying to an operator a GUI image representing the 3D inner surface profile of the pipe under inspection responsive to the GUI image data signal.

\* \* \* \* \*